(12) United States Patent
Yamazaki

(10) Patent No.: US 11,915,413 B2
(45) Date of Patent: Feb. 27, 2024

(54) ENDOSCOPE SYSTEM AND METHOD OF CONTROLLING ENDOSCOPE SYSTEM

(71) Applicant: OLYMPUS CORPORATION, Tokyo (JP)

(72) Inventor: Kenji Yamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 738 days.

(21) Appl. No.: 17/060,509

(22) Filed: Oct. 1, 2020

(65) Prior Publication Data
US 2021/0113058 A1 Apr. 22, 2021

Related U.S. Application Data

(63) Continuation of application No. PCT/JP2019/010619, filed on Mar. 14, 2019.

(30) Foreign Application Priority Data

Apr. 24, 2018 (JP) .................................. 2018-083282

(51) Int. Cl.
| | |
|---|---|
| G06T 7/00 | (2017.01) |
| A61B 1/00 | (2006.01) |
| G06T 7/90 | (2017.01) |
| A61B 1/04 | (2006.01) |

(Continued)

(52) U.S. Cl.
CPC ........ *G06T 7/0012* (2013.01); *A61B 1/00006* (2013.01); *A61B 1/04* (2013.01);
(Continued)

(58) Field of Classification Search
CPC .......................................... G06T 2207/30028
See application file for complete search history.

(56) References Cited

U.S. PATENT DOCUMENTS

2002/0177780 A1* 11/2002 Sendai ............... A61B 1/00186
600/476
2012/0253157 A1* 10/2012 Yamaguchi .......... A61B 1/0646
600/328

(Continued)

FOREIGN PATENT DOCUMENTS

| EP | 2 505 140 A1 | 10/2012 |
|---|---|---|
| EP | 2 789 288 A1 | 10/2014 |

(Continued)

OTHER PUBLICATIONS

International Search Report dated Jun. 11, 2019 received in PCT/JP2019/010619.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope system includes a light source apparatus, an illumination-light setting section capable of setting, as illumination light for illuminating an object including a biological tissue, first illumination light obtained by combining light in one or more wavelength bands selected from the light in plural wavelength bands and second illumination light obtained by combining light in one or more wavelength bands different from the first illumination light, selected out of the light in the plural wavelength bands, a light-source control section, and an image analyzing section configured to acquire an analysis result related to presence or absence of an abnormal finding. The illumination-light setting section sets, based on the analysis result of the image analyzing section for the first image acquired by the first illumination light, a combination of light in wavelength bands included in the second illumination light to be irradiated next.

19 Claims, 7 Drawing Sheets

(51) Int. Cl.
  *A61B 1/06*  (2006.01)
  *A61B 1/05*  (2006.01)
  *A61B 1/07*  (2006.01)

(52) U.S. Cl.
  CPC .......... *A61B 1/0638* (2013.01); *A61B 1/0655* (2022.02); *G06T 7/90* (2017.01); *A61B 1/05* (2013.01); *A61B 1/0669* (2013.01); *A61B 1/07* (2013.01); *G06T 2207/10068* (2013.01); *G06T 2207/10152* (2013.01)

(56) References Cited

U.S. PATENT DOCUMENTS

| | | | |
|---|---|---|---|
| 2012/0296205 A1* | 11/2012 | Chernov | A61B 18/1445 600/431 |
| 2014/0270499 A1 | 9/2014 | Kono et al. | |
| 2015/0297066 A1 | 8/2015 | Yanagidate | |
| 2016/0007830 A1 | 1/2016 | Chun | |
| 2018/0214009 A1 | 8/2018 | Endo | |
| 2020/0323433 A1* | 10/2020 | Ming | A61B 5/0086 |

FOREIGN PATENT DOCUMENTS

| | | |
|---|---|---|
| EP | 2 979 617 A1 | 2/2016 |
| EP | 3 357 402 A1 | 8/2018 |
| JP | 2012-000160 A | 1/2012 |
| JP | 2012-213550 A | 11/2012 |
| JP | 2015-204960 A | 11/2015 |
| JP | 2016-059402 A | 4/2016 |
| JP | 6247610 B2 | 12/2017 |
| WO | 2013/085061 A1 | 6/2013 |
| WO | 2014/156937 A1 | 10/2014 |
| WO | 2017/057392 A1 | 4/2017 |

* cited by examiner

ENDOSCOPE SYSTEM AND METHOD OF CONTROLLING ENDOSCOPE SYSTEM

CROSS REFERENCE TO RELATED APPLICATION

This application is a continuation application of PCT/JP2019/010619 filed on Mar. 14, 2019 and claims benefit of Japanese Application No. 2018-083282 filed in Japan on Apr. 24, 2018, the entire contents of which are incorporated herein by this reference.

BACKGROUND OF THE INVENTION

Field of the Invention

The present invention relates to an endoscope system and a method of controlling the endoscope system and, more particularly, to an endoscope system and a method of controlling the endoscope system used for observation of a biological tissue.

Description of the Related Art

In an endoscopic observation in a medical field, a technique for irradiating illumination light having a specific wavelength on an object including an abnormal finding such as reddening present in a subject and performing observation has been known.

More specifically, for example, Japanese Patent No. 6247610 discloses a configuration for, in an endoscope system, when the endoscope system is set in a high image quality mode, generating an image for display using an image signal obtained by picking up an image of a suspected lesion on which blue limited light and red light are irradiated and an image signal obtained by picking up an image of the suspected lesion on which violet light and green light are irradiated.

SUMMARY OF THE INVENTION

An endoscope system according to an aspect of the present invention includes: a light source apparatus configured to be able to emit light in a plurality of wavelength bands; an illumination-light setting section configured to be able to set, as illumination light for illuminating an object including a biological tissue present in a subject, first illumination light obtained by combining light in one or more wavelength bands selected out of the light in the plurality of wavelength bands and second illumination light obtained by combining light in one or more wavelength bands different from the first illumination light, selected out of the light in the plurality of wavelength bands; a light-source control section configured to control the light source apparatus in order to alternately irradiate, from the light source apparatus, the first illumination light and the second illumination light set by the illumination-light setting section; an image pickup section configured to pick up an image of return light from the object on which the illumination light is irradiated; and an image analyzing section configured to acquire an analysis result related to presence or absence of an abnormal finding by analyzing an image obtained by the image pickup section when the first illumination light is irradiated. The illumination-light setting section sets, based on the analysis result of the image analyzing section for the image acquired by the image pickup section when the first illumination light is irradiated, a combination of light in wavelength bands included in the second illumination light to be irradiated next.

An endoscope system according to an aspect of the present invention includes: a light source apparatus configured to be able to emit light in a plurality of wavelength bands; an illumination-light setting section configured to be able to select, as illumination light for illuminating an object including a biological tissue present in a subject, light in combinations of one or more wavelength bands out of the light in the plurality of wavelength bands and set first illumination light and second illumination light formed by differentiating a ratio of the light in the combinations; a light-source control section configured to control the light source apparatus in order to alternately irradiate, from the light source apparatus, the first illumination light and the second illumination light set by the illumination-light setting section; an image pickup section configured to pick up an image of return light from the object on which the illumination light is irradiated; and an image analyzing section configured to acquire an analysis result related to presence or absence of an abnormal finding by analyzing a first image obtained by the image pickup section when the first illumination light is irradiated. The illumination-light setting section sets, based on the analysis result of the image analyzing section for the first image acquired by the image pickup section when the first illumination light is irradiated, a light amount ratio of the light in the plurality of wavelength bands included in the second illumination light to be irradiated next.

A method of controlling an endoscope system according to an aspect of the present invention includes: irradiating, on an object including a biological tissue present in a subject, first illumination light obtained by selectively combining light in a plurality of wavelength bands; picking up an image of return light from the object on which the first illumination light is irradiated and acquiring a first image; acquiring an analysis result relating to presence or absence of an abnormal finding by analyzing the first image; irradiating, based on the analysis result, on the object, second illumination light obtained by selectively combining the light in the plurality of wavelength bands to be different from the light combined to be the first illumination light; picking up an image of return light from the object on which the second illumination light is irradiated and acquiring a second image; and repeatedly executing the respective operations described above.

DETAILED DESCRIPTION OF THE PREFERRED EMBODIMENTS

Embodiments of the present invention are explained below with reference to the drawings.

First Embodiment

FIG. 1 to FIG. 5 relate to a first embodiment of the present invention.

Figure 1:
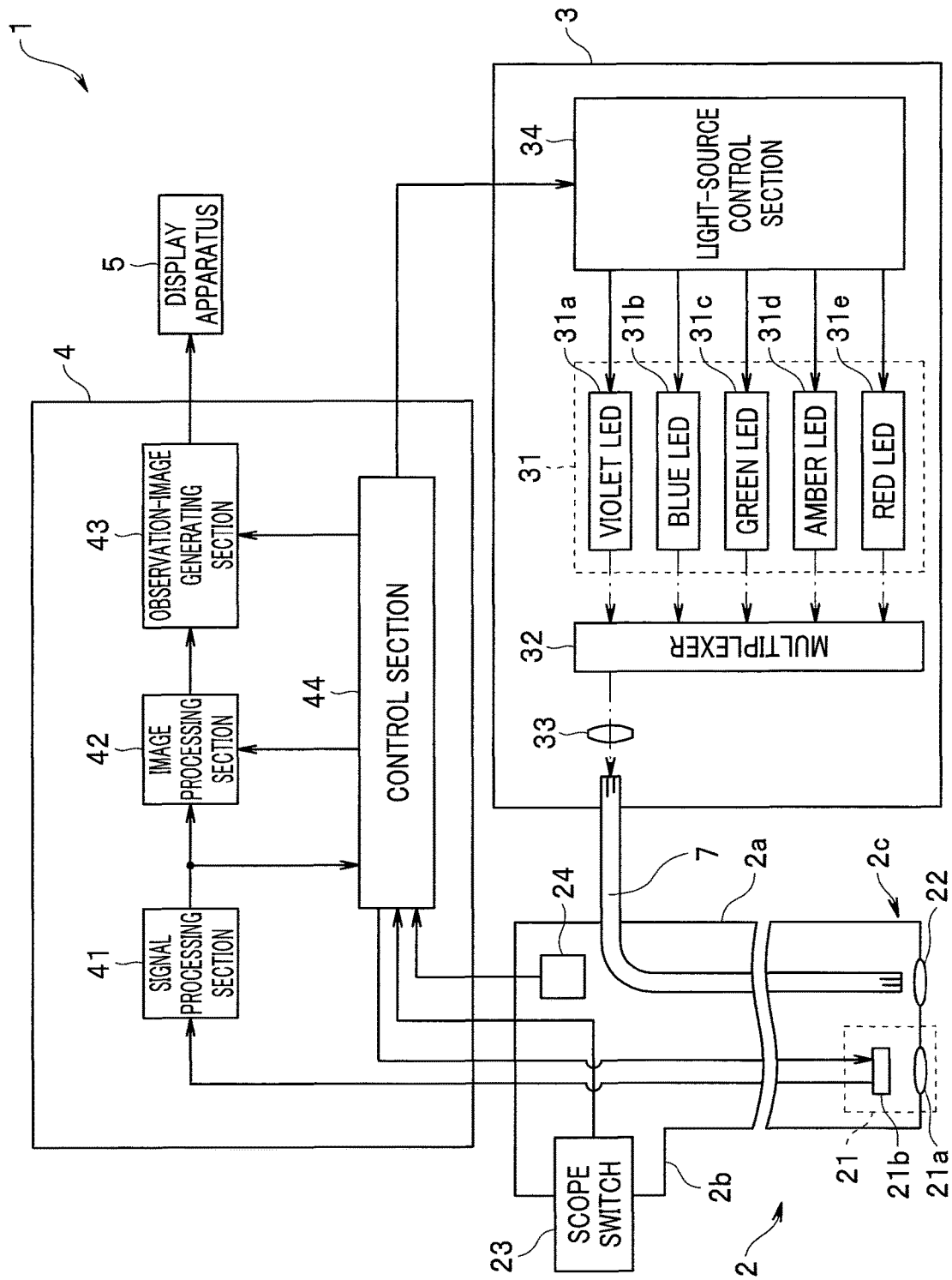
FIG. 1 is a diagram showing a configuration of a main part of an endoscope system according to an embodiment.

An endoscope system 1 includes, as shown in FIG. 1, an endoscope 2 insertable into a subject and configured to pick up an image of an object such as a biological tissue present in the subject and output an image pickup signal, a light source apparatus 3 configured to supply illumination light used for observation of the object via a light guide 7 inserted through and disposed inside the endoscope 2, a processor 4 configured to generate and output an observation image or the like corresponding to the image pickup signal outputted from the endoscope 2, and a display apparatus 5 configured to display the observation image outputted from the processor 4 on a screen. FIG. 1 is a diagram showing a configuration of a main part of an endoscope system according to the embodiment.

The endoscope 2 includes an insertion section 2a formed in an elongated shape insertable into the subject and an operation section 2b provided on a proximal end side of the insertion section 2a. The endoscope 2 is configured to be detachably connected to the processor 4 via, for example, a universal cable (not illustrated) incorporating a signal line used for transmission of various signals such as an image pickup signal outputted from an image pickup section 21 (explained below). The endoscope 2 is configured to be detachably connected to the light source apparatus 3 via a light guide cable (not illustrated) incorporating at least a part of the light guide 7.

At a distal end portion 2c of the insertion section 2a, an image pickup section 21 for picking up an image of an object including a biological tissue present in a subject, an emission end portion of the light guide 7, and an illumination optical system 22 that irradiates illumination light transmitted by the light guide 7 onto the object are provided.

The image pickup section 21 is configured to pick up an image of return light from the object on which the illumination light from the illumination optical system 22 is irradiated and output an image pickup signal. More specifically, the image pickup section 21 includes an objective optical system 21a configured to form an image of the return light emitted from the object on which the illumination light from the illumination optical system 22 is irradiated and an image pickup device 21b configured to generate an image pickup signal by picking up an image of the return light, the image of which is formed by the objective optical system 21a, and output the generated image pickup signal to the processor 4.

The image pickup device 21b includes, for example, an image sensor such as a CCD or a CMOS. On an image pickup surface of the image pickup device 21b, a color filter having primary color Bayer array for splitting the return light made incident from the objective optical system 21a into three colors of red, green, and blue and a plurality of pixels disposed in a matrix shape in order to pick up an image of light passed through the color filter are provided. The image pickup device 21b is configured to perform operation corresponding to a control signal outputted from the processor 4.

The operation section 2b has a shape for enabling a user to grip and operate the operation section 2b. In the operation section 2b, a scope switch 23 including one or more switches capable of giving an instruction corresponding to input operation of the user to the processor 4 is provided.

Inside the operation section 2b, a scope memory 24 storing endoscope information including information specific to the endoscope 2 such as a model of the endoscope 2 is provided. Note that the endoscope information stored in the scope memory 24 is read out by a control section 44 (explained below) of the processor 4 when the endoscope 2 and the processor 4 are electrically connected and a power supply of the processor 4 is turned on.

The light source apparatus 3 has a function of a light source section and is configured to be able to generate light in a plurality of wavelength bands different from one another and able to alternately generate illumination light EL1 and illumination light EL2 (both of which are explained below) as illumination light for illuminating an object including a biological tissue present in a subject. The light source apparatus 3 includes a light emitting section 31, a multiplexer 32, a condensing lens 33, and a light-source control section 34.

The light emitting section 31 includes a violet LED 31a, a blue LED 31b, a green LED 31c, an amber LED 31d, and a red LED 31e. The respective LEDs of the light emitting section 31 are configured to individually emit and turn off light according to control by the light-source control section 34. The respective LEDs of the light emitting section 31 is configured to emit light with a light emission amount corresponding to the control by the light-source control section 34.

Figure 2:
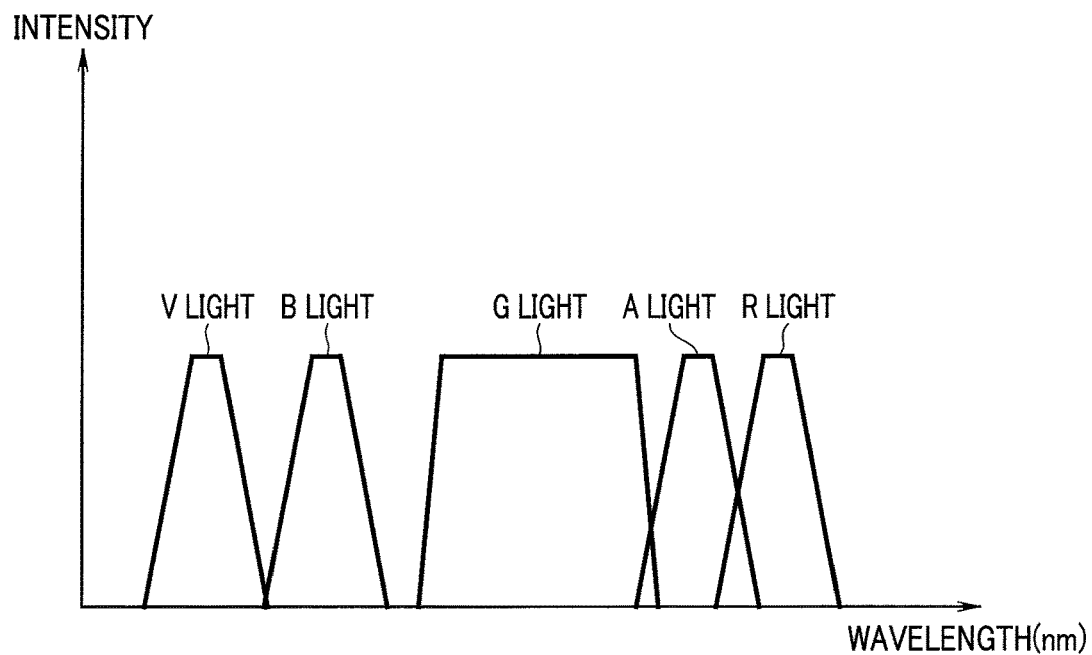
FIG. 2 is a diagram showing an example of wavelength bands of light emitted from respective LEDs provided in a light source apparatus of the endoscope system according to the embodiment.

The violet LED 31a is configured to generate violet light (hereinafter referred to as V light) having a center wavelength in a violet region. More specifically, the violet LED 31a is configured to generate, as the V light, for example, light, a center wavelength of which is set to any wavelength of 400 nm to 420 nm shown in FIG. 2. Note that a light emission amount of the violet LED 31a is defined as a total light amount obtained by integrating intensities of light having respective wavelengths included in a wavelength band of the V light. FIG. 2 is a diagram showing an example of wavelength bands of light emitted from the respective LEDs provided in the light source apparatus of the endoscope system according to the embodiment.

The blue LED 31b is configured to generate blue light (hereinafter referred to as B light) having a center wavelength in a blue region on a longer wavelength side relative to the V light. More specifically, the blue LED 31b is configured to generate, as the B light, for example, light, a center wavelength of which is set to any wavelength of 440 nm to 470 nm shown in FIG. 2. Note that a light emission amount of the blue LED 31b is defined as a total light amount obtained by integrating intensities of light having respective wavelengths included in a wavelength band of the B light.

The green LED 31*c* is configured to generate green light (hereinafter referred to as G light) having a center wavelength in a green region on the longer wavelength side relative to the B light. More specifically, the green LED 31*c* is configured to generate, as the G light, for example, light, a center wavelength of which is set to any wavelength of 510 nm to 580 nm shown in FIG. 2. Note that a light emission amount of the green LED 31*c* is defined as a total light amount obtained by integrating intensities of light having respective wavelengths included in a wavelength band of the G light.

The amber LED 31*d* is configured to generate amber light (hereinafter referred to as A light) having a center wavelength in an amber region on the longer wavelength side relative to the G light. More specifically, the amber LED 31*d* is configured to generate, as the A light, for example, light, a center wavelength of which is set to any wavelength of 590 nm to 610 nm shown in FIG. 2. Note that a light emission amount of the amber LED 31*d* is defined as a total light amount obtained by integrating intensities of light having respective wavelengths included in a wavelength band of the A light.

The red LED 31*e* is configured to generate red light (hereinafter referred to as R light) having a center wavelength in a red region on the longer wavelength side relative to the A light. More specifically, the red LED 31*e* is configured to generate, as the R light, for example, light, a center wavelength of which is set to any wavelength of 620 nm to 660 nm shown in FIG. 2. Note that a light emission amount of the red LED 31*e* is defined as a total light amount obtained by integrating intensities of light having respective wavelengths included in a wavelength band of the R light.

The multiplexer 32 is configured to be able to multiplex the respective light emitted from the light emitting section 31 and make multiplexed light incident on the condensing lens 33.

The condensing lens 33 is configured to condense the light made incident through the multiplexer 32 and emit the light to an incident end portion of the light guide 7.

The light-source control section 34 includes, for example, a control circuit. The light-source control section 34 is configured to drive the respective LEDs of the light emitting section 31 according to a control signal outputted from the processor 4.

The processor 4 includes a signal processing section 41, an image processing section 42, an observation-image generating section 43, and a control section 44.

The signal processing section 41 includes, for example, a signal processing circuit. The signal processing section 41 is configured to generate image data by applying predetermined signal processing such as A/D conversion to an image pickup signal outputted from the endoscope 2 and output the generated image data respectively to the image processing section 42 and the control section 44 frame by frame.

The image processing section 42 includes, for example, an image processing circuit. The image processing section 42 is configured to perform, based on the image data outputted from the signal processing section 41 and a control signal outputted from the control section 44, processing for respectively generating image data IDV of a violet component corresponding to the V light included in return light of illumination light irradiated on an object, image data IDB of a blue component corresponding to the B light included in the return light, image data IDG of a green component corresponding to the G light included in the return light, image data IDA of an amber component corresponding to the A light included in the return light, and image data IDR of a red component corresponding to the R light included in the return light. The image processing section 42 is configured to apply predetermined image processing to the image data of the respective color components generated as explained above and output the image data to the observation-image generating section 43.

The observation-image generating section 43 includes, for example, an image generation circuit. The observation-image generating section 43 is configured to generate, based on a control signal outputted from the control section 44, an observation image using the image data outputted from the image processing section 42 and output the generated observation image to the display apparatus 5 frame by frame.

The control section 44 includes, for example, a control circuit. The control section 44 is configured to generate and output a control signal for causing the image processing section 42 and the observation-image generating section 43 to perform operation corresponding to an instruction from the scope switch 23. The control section 44 is configured to generate and output a control signal for controlling operation of the image pickup device 21*b*. The control section 44 is configured to read endoscope information stored in the scope memory 24 when the endoscope 2 and the processor 4 are electrically connected and the power supply of the processor 4 is turned on.

Figure 3:
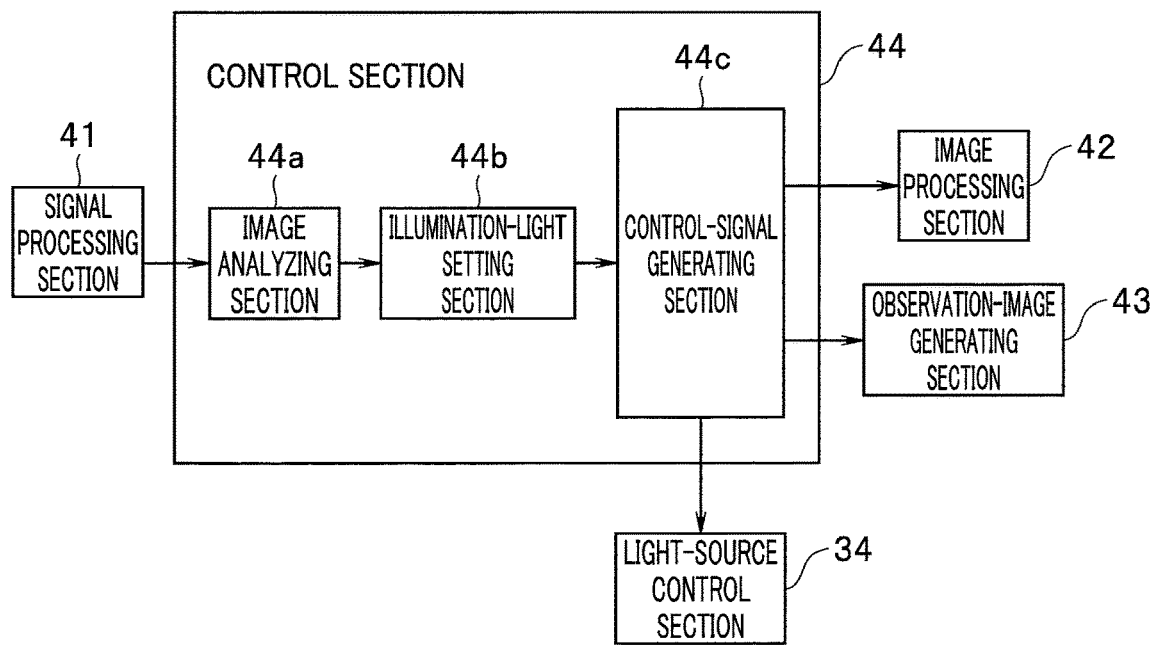
FIG. 3 is a diagram for explaining an example of a configuration of a control section provided in a processor of the endoscope system according to the embodiment.

The control section 44 is configured to generate a control signal for causing the light-source control section 34 to alternately generate the illumination light EL1 and the illumination light EL2 and output the control signal to the light-source control section 34. The control section 44 is configured to generate control signals for causing the image processing section 42 and the observation-image generating section 43 to perform operation corresponding to the illumination light EL1 and EL2 and output the control signals respectively to the image processing section 42 and the observation-image generating section 43. The control section 44 includes, for example, as shown in FIG. 3, an image analyzing section 44*a*, an illumination-light setting section 44*b*, and a control-signal generating section 44*c*. FIG. 3 is a diagram for explaining an example of a configuration of a control section provided in a processor of the endoscope system according to the embodiment.

The image analyzing section 44*a* is configured to apply analysis processing to image data outputted from the signal processing section 41 according to irradiation of the illumination light EL1 and output analysis result information indicating an analysis result obtained by the analysis processing to the illumination-light setting section 44*b*. Note that a specific example of operation performed in the image analyzing section 44*a* is explained below.

The illumination-light setting section 44*b* is configured to set, as the illumination light EL1, light of predetermined one or more colors selected out of the light (the V light, the B light, the G light, the A light, and the R light) of the five colors emitted from the respective LEDs of the light emitting section 31. The illumination-light setting section 44*b* is configured to select, based on the analysis result information outputted from the image analyzing section 44*a*, light of one or more colors out of the light of the five colors emitted from the respective LEDs of the light emitting section 31 and set the selected light of the one or more colors as the illumination light EL2. The illumination-light setting section 44*b* is configured to be able to perform processing for comparing an analysis result indicated by latest analysis result information outputted from the image analyzing section 44*a* and an analysis result indicated by analysis result information in the past stored in a not-shown memory or the like. The illumination-light setting section 44b is configured to alternately output, to the control-signal generating section 44c, illumination light setting information indicating setting content of the illumination light EL1 and illumination light setting information indicating setting content of the illumination light EL2. Note that a specific example of operation performed in the illumination-light setting section 44b is explained below.

The control-signal generating section 44c is configured to alternately generate, based on the illumination light setting information outputted from the illumination-light setting section 44b, a control signal for causing the light-source control section 34 to generate the illumination light EL1 and a control signal for causing the light-source control section 34 to generate the illumination light EL2 explained below and output the control signals to the light-source control section 34. The control-signal generating section 44c is configured to generate, based on the illumination light setting information outputted from the illumination-light setting section 44b, control signals for causing the image processing section 42 and the observation-image generating section 43 to perform operations corresponding to the illumination light EL1 and EL2 and output the control signals respectively to the image processing section 42 and the observation-image generating section 43. Note that a specific example of operation performed in the control-signal generating section 44c is explained below.

In this embodiment, the control-signal generating section 44c only has to generate a control signal for setting switching speed in causing the light-source control section 34, the image processing section 42, and the observation-image generating section 43 to alternately generate the illumination light EL1 and EL2 to a double of a setting value of a frame rate in displaying an observation image on the display apparatus 5 and output the control signal respectively to the light-source control section 34, the image processing section 42, and the observation-image generating section 43. More specifically, the control-signal generating section 44c only has to generate, based on the illumination light setting information outputted from the illumination-light setting section 44b, for example, a control signal for causing the light-source control section 34 to switch the illumination light EL1 and EL2 at every $\frac{1}{60}$ second and, at the same time, generate the illumination light EL1 and EL2 and output the control signal to the light-source control section 34 and generate, based on the illumination light setting information, a control signal for causing the image processing section 42 and the observation-image generating section 43 to output the observation image to the display apparatus 5 at 30 fps and output the control signal to the image processing section 42 and the observation-image generating section 43.

Note that, in this embodiment, for example, the respective sections of the processor 4 may be configured as individual electronic circuits or may be configured as circuit blocks in an integrated circuit such as an FPGA (field programmable gate array). In this embodiment, for example, the processor 4 may include one or more CPUs. The configuration according to this embodiment may be modified as appropriate, whereby, for example, the processor 4 reads, from a storage medium (not illustrated) such as a memory, a program for causing the signal processing section 41, the image processing section 42, the observation-image generating section 43, and the control section 44 to execute the functions of the signal processing section 41, the image processing section 42, the observation-image generating section 43, and the control section 44 and performs operation corresponding to the read program.

The display apparatus 5 includes, for example, an LCD (liquid crystal display) and is configured to be able to display an observation image and the like outputted from the processor 4.

Figure 4:
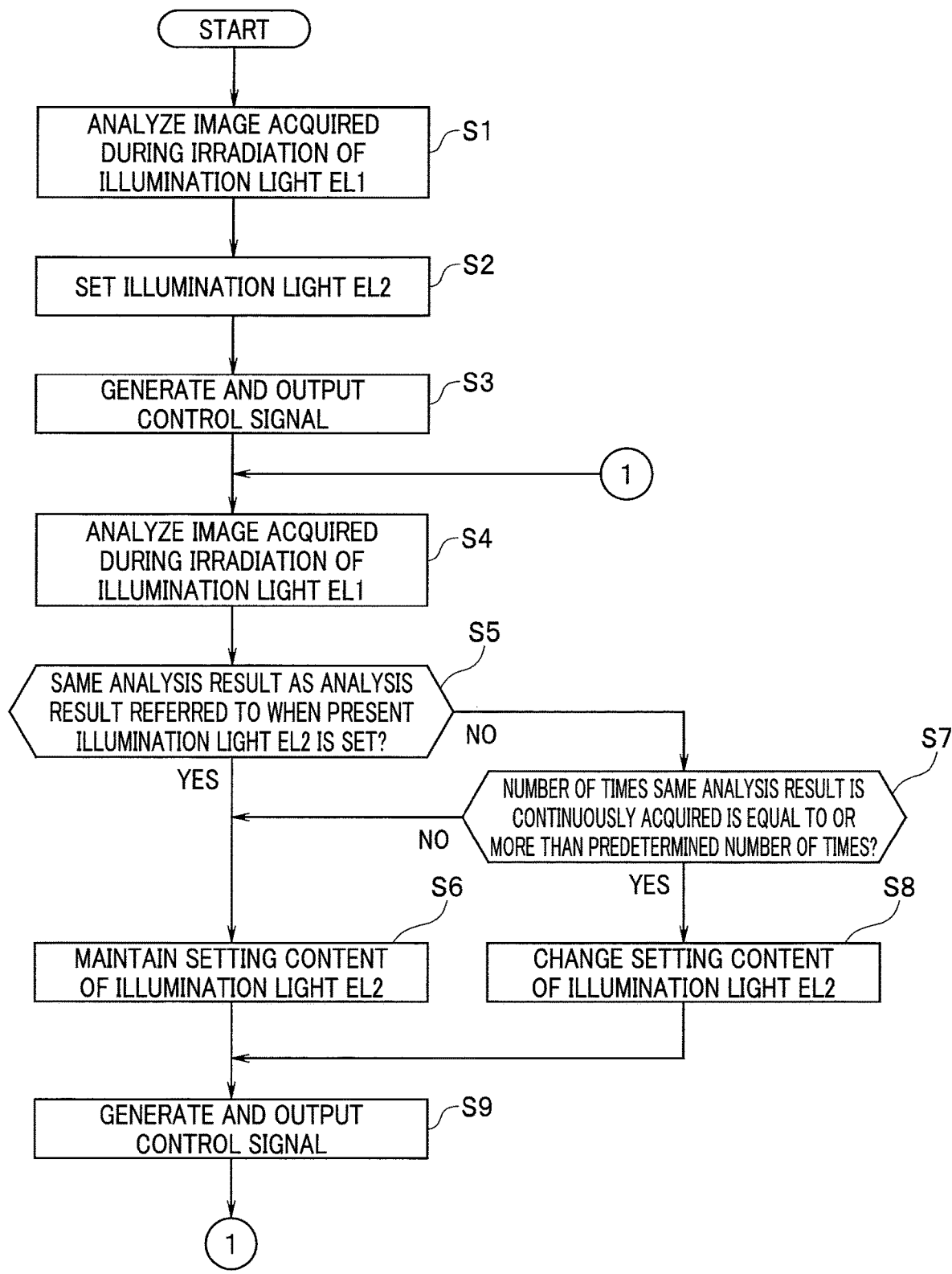
FIG. 4 is a flowchart showing an overview of operation performed in the endoscope system according to the embodiment.
Figure 5:
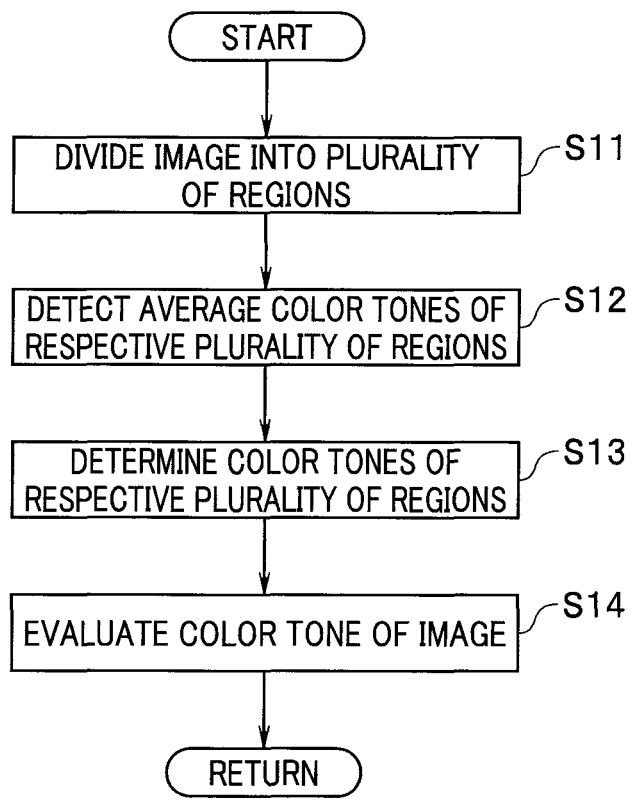
FIG. 5 is a flowchart for explaining a specific example of analysis processing performed in an endoscope system according to a first embodiment.

Subsequently, action of this embodiment is explained with reference to FIG. 4 and FIG. 5. FIG. 4 is a flowchart showing an overview of operation performed in the endoscope system according to the embodiment. FIG. 5 is a flowchart for explaining a specific example of analysis processing performed in the endoscope system according to the first embodiment.

For example, when an instruction for starting observation by the endoscope 2 is performed according to operation of the scope switch 23 by the user, the illumination-light setting section 44b sets, as the illumination light EL1, the G light and the R light selected out of the light of the five colors emitted from the respective LEDs of the light emitting section 31 and outputs illumination light setting information ESA indicating setting content of the illumination light EL1 to the control-signal generating section 44c. Note that, in this embodiment, the illumination-light setting section 44b may set the B light, the G light, and the R light as the illumination light EL1.

The control-signal generating section 44c generates, based on the illumination light setting information ESA outputted from the illumination-light setting section 44b, a control signal for causing the light-source control section 34 to generate the illumination light EL1 and outputs the control signal to the light-source control section 34. The control-signal generating section 44c generates, based on the illumination light setting information ESA outputted from the illumination-light setting section 44b, a control signal for causing the image processing section 42 to stop generation of image data of respective color components corresponding to return light of the illumination light EL1 and outputs the control signal to the image processing section 42. The control-signal generating section 44c generates, based on the illumination light setting information ESA outputted from the illumination-light setting section 44b, a control signal for causing the observation-image generating section 43 to stop generation of an observation image in an irradiation period of the illumination light EL1 and outputs the control signal to the observation-image generating section 43.

According to the operations of the illumination-light setting section 44b and the control-signal generating section 44c explained above, the illumination light EL1 including the G light and the R light is irradiated on an object including a biological tissue, an image pickup signal obtained by picking up an image of return light from the object is outputted from the image pickup section 21, and image data ID1 generated according to the image pickup signal is outputted from the signal processing section 41.

The image analyzing section 44a applies analysis processing to the image data ID1 equivalent to an image acquired during the irradiation of the illumination light EL1 and outputs analysis result information ARA indicating an analysis result obtained by the analysis processing to the illumination-light setting section 44b (step S1 in FIG. 4).

A specific example of the analysis processing performed by the image analyzing section 44a in this embodiment is explained below with reference to FIG. 5.

The image analyzing section 44a performs processing for dividing the image data ID1 outputted from the signal processing section 41 into a plurality of regions (step S11 in FIG. 5). According to such processing, for example, the image data ID1 outputted from the signal processing section 41 is divided into n (n≥2) regions Hi (1≤i≤n).

The image analyzing section 44a performs processing for detecting average color tones of the respective plurality of regions Hi obtained through the processing in step S11 in FIG. 5 (step S12 in FIG. 5).

More specifically, the image analyzing section 44a performs, for example, processing for calculating arithmetic operation values CVA by performing an arithmetic operation of the following Equation (1) in respective s pixels excluding a pixel in which halation occurs from all the pixels included in one region Hi and detecting, as a value indicating an average color tone of the one region Hi, an average AVA of the arithmetic operation values CVA calculated in the respective s pixels. The image analyzing section 44a acquires, as a detection result of average color tones of the respective plurality of regions Hi, a calculation result of the average AVA in the respective plurality of regions Hi obtained by repeatedly performing the processing n times.

$$CVA = 32 \times \log_2(Rp/Gp) \quad (1)$$

The image analyzing section 44a performs, based on the detection result of the average color tones of the respective plurality of regions Hi obtained through the processing in step S12 in FIG. 5, processing for judging color tones of the respective plurality of regions Hi (step S13 in FIG. 5).

More specifically, for example, when the average AVA calculated in one region Hi is smaller than a threshold THA, the image analyzing section 44a acquires a judgement result indicating that a color tone of the one region Hi is a red tone having low chroma. For example, when the average AVA calculated in one region Hi is larger than a threshold THB (>THA), the image analyzing section 44a acquires a judgement result indicating that a color tone of the one region Hi is a red tone having high chroma. For example, when the average AVA calculated in one region Hi belongs to a range of the threshold THA or more and the threshold THB or less, the image analyzing section 44a acquires a judgement result indicating that a color tone of the one region Hi is a red tone having medium chroma.

The image analyzing section 44a performs, based on judgement results of the color tones of the respective plurality of regions Hi obtained through the processing in step S13 in FIG. 5, processing for evaluating a color tone of the image data ID1 that is a processing target in step S11 in FIG. 5 (step S14 in FIG. 5).

More specifically, for example, when the number of regions Hi judged as the red tone having low chroma among n regions Hi obtained by dividing the image data ID1 is larger than n/2 (occupies a majority), the image analyzing section 44a acquires an evaluation result indicating that the color tone of the image data ID1 is equivalent to a color tone of a discolored mucous membrane. For example, when the number of regions Hi judged as the red tone having high chroma among the n regions Hi obtained by dividing the image data ID1 is larger than n/2 (occupies the majority), the image analyzing section 44a acquires an evaluation result indicating that the color tone of the image data ID1 is equivalent to a color tone of a reddened mucous membrane. For example, when the number of regions Hi judged as the red tone having medium chroma among the n regions Hi obtained by dividing the image data ID1 is larger than n/2 (occupies the majority), the image analyzing section 44a acquires an evaluation result indicating that the color tone of the image data ID1 is equivalent to a color tone of a normal mucous membrane. For example, when all of the number of regions Hi judged as the red tone having high chroma, the number of regions Hi judged as the red tone having high chroma, and the number of regions Hi judged as the red tone having medium chroma are equal to or smaller than n/2 (less than the majority) in the n regions Hi obtained by dividing the image data ID1, the image analyzing section 44a acquires an evaluation result indicating that the color tone of the image data ID1 is equivalent to the color tone of the normal mucous membrane.

In other words, the image analyzing section 44a in this embodiment applies the analysis processing shown in the flowchart of FIG. 5 to the image data ID1 outputted from the signal processing section 41, acquires an evaluation result relating to the color tone of the image data ID1 as an analysis result of the analysis processing, and outputs the analysis result information ARA indicating the acquired analysis result to the illumination-light setting section 44b. The image analyzing section 44a in this embodiment analyzes the image data ID1 obtained by picking up an image of the object including the biological tissue during the irradiation of the illumination light EL1 to thereby acquire, as an analysis result relating to presence or absence of an abnormal finding in the image data ID1, an evaluation result relating to which of a color tone equivalent to the abnormal finding and a color tone equivalent to a normal finding the color tone of the image data ID1 belongs.

The illumination-light setting section 44b sets, based on the analysis result information ARA outputted from the image analyzing section 44a, as the illumination light EL2, light of one or more colors selected out of the light of the five colors emitted from the respective LEDs of the light emitting section 31 (step S2 in FIG. 4) and outputs illumination light setting information ESB indicating setting content of the illumination light EL2 to the control-signal generating section 44c.

More specifically, the illumination-light setting section 44b sets, based on the analysis result information ARA outputted from the image analyzing section 44a, for example, when detecting that the color tone of the image data ID1 is equivalent to the color tone of the discolored mucous membrane, as the illumination light EL2, the V light, the G light, and the R light selected out of the light of the five colors emitted from the respective LEDs of the light emitting section 31 and outputs the illumination light setting information ESB indicating the setting content of the illumination light EL2 to the control-signal generating section 44c. The illumination-light setting section 44b sets, based on the analysis result information ARA outputted from the image analyzing section 44a, for example, when detecting that the color tone of the image data ID1 is equivalent to the color tone of the reddened mucous membrane, as the illumination light EL2, the B light, the G light, and the A light selected out of the light of the five colors emitted from the respective LEDs of the light emitting section 31 and outputs the illumination light setting information ESB indicating the setting content of the illumination light EL2 to the control-signal generating section 44c. The illumination-light setting section 44b sets, based on the analysis result information ARA outputted from the image analyzing section 44a, for example, when detecting that the color tone of the image data ID1 is equivalent to the color tone of the normal mucous membrane, as the illumination light EL2, the B light, the G light, and the R light selected out of the light of the five colors emitted from the respective LEDs of the light emitting section 31 and outputs the illumination light setting information ESB indicating the setting content of the illumination light EL2 to the control-signal generating section 44c.

In other words, the illumination-light setting section 44b in this embodiment combines light in one or more wavelength bands selected out of the light of the five colors emitted from the respective LEDs of the light emitting section 31 and sets the light as the illumination light EL2 such that the illumination light EL2 has a different wavelength band according to the analysis result indicated by the analysis result information ARA outputted from the image analyzing section 44a.

The control-signal generating section 44c generates, based on the illumination light setting information ESB outputted from the illumination-light setting section 44b, a control signal for causing the light-source control section 34 to generate the illumination light EL2 and outputs the control signal to the light-source control section 34 (step S3 in FIG. 4). The control-signal generating section 44c generates, based on the illumination light setting information ESB outputted from the illumination-light setting section 44b, a control signal for causing the image processing section 42 to generate image data of respective color components corresponding to return light of the illumination light EL2 and outputs the control signal to the image processing section 42 (step S3 in FIG. 4). The control-signal generating section 44c generates, based on the illumination light setting information ESB outputted from the illumination-light setting section 44b, a control signal for causing the observation-image generating section 43 to generate an observation image using image data of respective color components outputted from the image processing section 42 during irradiation of the illumination light EL2 and outputs the control signal to the observation-image generating section 43 (step S3 in FIG. 4).

According to the operations of the illumination-light setting section 44b and the control-signal generating section 44c explained above, for example, when the color tone of the image data ID1 is equivalent to the color tone of the discolored mucous membrane, the illumination light EL2 including the V light, the G light, and the R light is irradiated on an object including a biological tissue, an image pickup signal obtained by picking up an image of return light from the object is outputted from the image pickup section 21, and image data ID2 generated according to the image pickup signal is outputted from the signal processing section 41. According to the operations of the illumination-light setting section 44b and the control-signal generating section 44c explained above, for example, when the color tone of the image data ID1 is equivalent to the color tone of the reddened mucous membrane, the illumination light EL2 including the B light, the G light, and the A light is irradiated on an object including a biological tissue, an image pickup signal obtained by picking up an image of return light from the object is outputted from the image pickup section 21, and the image data ID2 generated according to the image pickup signal is outputted from the signal processing section 41. According to the operations of the illumination-light setting section 44b and the control-signal generating section 44c explained above, for example, when the color tone of the image data ID1 is equivalent to the color tone of the normal mucous membrane, the illumination light EL2 including the B light, the G light, and the R light is irradiated on an object including a biological tissue, an image pickup signal obtained by picking up an image of return light from the object is outputted from the image pickup section 21, and the image data ID2 generated according to the image pickup signal is outputted from the signal processing section 41.

The image processing section 42 respectively generates, based on the image data ID2 outputted from the signal processing section 41 and a control signal outputted from the control-signal generating section 44c, for example, when the color tone of the image data ID1 is equivalent to the color tone of the discolored mucous membrane, image data IDV2 of a violet component included in the image data ID2, image data IDG2 of a green component included in the image data ID2, and image data IDR2 of a red component included in the image data ID2, applies predetermined image processing to the generated respective image data, and outputs the image data to the observation-image generating section 43. The image processing section 42 respectively generates, based on the image data ID2 outputted from the signal processing section 41 and a control signal outputted from the control-signal generating section 44c, for example, when the color tone of the image data ID1 is equivalent to the color tone of the reddened mucous membrane, image data IDB2 of a blue component included in the image data ID2, image data IDG2 of a green component included in the image data ID2, and image data IDA2 of an amber component included in the image data ID2, applies predetermined image processing to the generated respective image data, and outputs the image data to the observation-image generating section 43. The image processing section 42 respectively generates, based on the image data ID2 outputted from the signal processing section 41 and a control signal outputted from the control-signal generating section 44c, for example, when the color tone of the image data ID1 is equivalent to the color tone of the normal mucous membrane, image data IDB2 of a blue component included in the image data ID2, image data IDG2 of a green component included in the image data ID2, and image data IDR2 of a red component included in the image data ID2, applies predetermined image processing to the generated respective image data, and outputs the image data to the observation-image generating section 43.

Based on a control signal outputted from the control section 44, for example, when the color tone of the image data ID1 is equivalent to the color tone of the discolored mucous membrane, the observation-image generating section 43 allocates the image data IDV2 to a B (blue) channel of the display apparatus 5, allocates the image data IDG2 to a G (green) channel of the display apparatus 5, and allocates the image data IDR2 to an R (red) channel of the display apparatus 5 to thereby generate an observation image KGA and outputs the generated observation image KGA to the display apparatus 5. Based on a control signal outputted from the control section 44, for example, when the color tone of the image data ID1 is equivalent to the color tone of the reddened mucous membrane, the observation-image generating section 43 allocates the image data IDB2 to the B channel of the display apparatus 5, allocates the image data IDG2 to the G channel of the display apparatus 5, and allocates the image data IDA2 to the R channel of the display apparatus 5 to thereby generate an observation image KGB and outputs the generated observation image KGB to the display apparatus 5. Based on a control signal outputted from the control section 44, for example, when the color tone of the image data ID1 is equivalent to the color tone of the normal mucous membrane, the observation-image generating section 43 allocates the image data IDB2 to the B channel of the display apparatus 5, allocates the image data IDG2 to the G channel of the display apparatus 5, and allocates the image data IDR2 to the R channel of the display apparatus 5 to thereby generate an observation image KGC and outputs the generated observation image KGC to the display apparatus 5.

After outputting the illumination light setting information ESB obtained through the processing in step S2 in FIG. 4 to the control-signal generating section 44c, the illumination-light setting section 44b outputs the illumination light setting information ESA to the control-signal generating section 44c again.

The control-signal generating section 44c generates, based on the illumination light setting information ESA outputted from the illumination-light setting section 44b, a control signal for causing the light-source control section 34 to generate the illumination light EL1 and outputs the control signal to the light-source control section 34. The control-signal generating section 44c generates, based on the illumination light setting information ESA outputted from the illumination-light setting section 44b, a control signal for causing the image processing section 42 to stop generation of images of respective color components corresponding to return light of the illumination light EL1 and outputs the control signal to the image processing section 42. The control-signal generating section 44c generates, based on the illumination light setting information ESA outputted from the illumination-light setting section 44b, in the irradiation period of the illumination light EL1, a control signal for causing the observation-image generating section 43 to stop generation of an observation image and outputs the control signal to the observation-image generating section 43.

The image analyzing section 44a applies analysis processing by the same method as step S1 in FIG. 4 to the image data ID1 equivalent to an image acquired during the irradiation of the illumination light EL1 and outputs, to the illumination-light setting section 44b, analysis result information ARB indicating an analysis result obtained by the analysis processing (step S4 in FIG. 4).

The illumination-light setting section 44b performs processing for judging whether an analysis result indicated by latest analysis result information ARBN equivalent to the analysis result information ARB obtained through the processing in step S4 in FIG. 4 is the same as an analysis result indicated by analysis result information ARBP in the past equivalent to the analysis result information ARA or ARB referred to when the present illumination light EL2 is set (step S5 in FIG. 4).

When acquiring a judgement result indicating that the analysis result indicated by the latest analysis result information ARBN is the same as the analysis result indicated by the analysis result information ARBP in the past (S5: YES), the illumination-light setting section 44b continues to perform processing in step S6 in FIG. 4 explained below. When acquiring a judgement result indicating that the analysis result indicated by the latest analysis result information ARBN is different from the analysis result indicated by the analysis result information ARBP in the past (S5: NO), the illumination-light setting section 44b continues to perform processing in step S7 in FIG. 4 explained below.

In order to maintain present setting content of the illumination light EL2, the illumination-light setting section 44b outputs, to the control-signal generating section 44c, the illumination light setting information ESB indicating the same setting content as the present setting content (step S6 in FIG. 4).

The illumination-light setting section 44b performs processing for judging whether the number of times the same analysis result as the analysis result indicated by the latest analysis result information ARBN is continuously acquired is equal to or more than a predetermined number of times (step S7 in FIG. 4).

When acquiring a judgement result indicating that the number of times the same analysis result as the analysis result indicated by the latest analysis result information ARBN is continuously acquired is less than the predetermined number of times (S7: NO), the illumination-light setting section 44b continues to perform the processing in step S6 in FIG. 4. When acquiring a judgement result indicating that the number of times the same analysis result as the analysis result indicated by the latest analysis result information ARBN is continuously acquired is equal to or more than the predetermined number of times (S7: YES), the illumination-light setting section 44b changes the setting content of the illumination light EL2 to setting content corresponding to the analysis result indicated by the latest analysis result information ARBN and outputs the illumination light setting information ESB indicating the setting content of the illumination light EL2 after the change to the control-signal generating section 44c (step S8 in FIG. 4).

The control-signal generating section 44c generates, based on the illumination light setting information ESB obtained through the processing in step S6 or S8 in FIG. 4, a control signal for causing the light-source control section 34 to generate the illumination light EL2 corresponding to the illumination light setting information ESB and outputs the control signal to the light-source control section 34 (step S9 in FIG. 4). The control-signal generating section 44c generates, based on the illumination light setting information ESB obtained through the processing in step S6 or step S8 in FIG. 4, control signals for causing the image processing section 42 and the observation-image generating section 43 to perform operation (relating to generation of an observation image) corresponding to the illumination light setting information ESB and outputs the control signals respectively to the image processing section 42 and the observation-image generating section 43 (step S9 in FIG. 4).

According to this embodiment, for example, according to the operation of the scope switch 23 by the user, the processing in step S4 to step S9 in FIG. 4 is repeatedly performed until an instruction to end the observation by the endoscope 2 is performed. According to this embodiment, a spectrum of the illumination light EL2 is set according to a color tone of the image data ID1 obtained when the illumination light EL1 set to a predetermined spectrum is irradiated on an object. An observation image corresponding to the illumination light EL2 is displayed on the display apparatus 5. According to this embodiment, for example, when an abnormal finding region ABF equivalent to a mucous membrane in which atrophy occurs is included in the image data ID1, the observation image KGA generated using the image data IDV2 corresponding to return light of the V light strongly scattered on a surface of the mucous membrane is displayed on the display apparatus 5 (as an observation image corresponding to the illumination light EL2). Therefore, it is possible to improve visibility of the abnormal finding region ABF. According to this embodiment, for example, when an abnormal finding region ABR equivalent to a mucous membrane in which diffuse reddening occurs is included in the image data ID1, the observation image KGB generated using the image data IDA2 corresponding to return light of the A light having an absorption coefficient to hemoglobin higher than an absorption coefficient of the R light is displayed on the display apparatus 5 (as an observation image corresponding to the illumination light EL2). Therefore, it is possible to improve visibility of the abnormal finding region ABR. Therefore, according to this embodiment, it is possible to reduce a burden on a surgeon who performs work relating to diagnosis of an abnormal finding.

Second Embodiment

Figure 6:
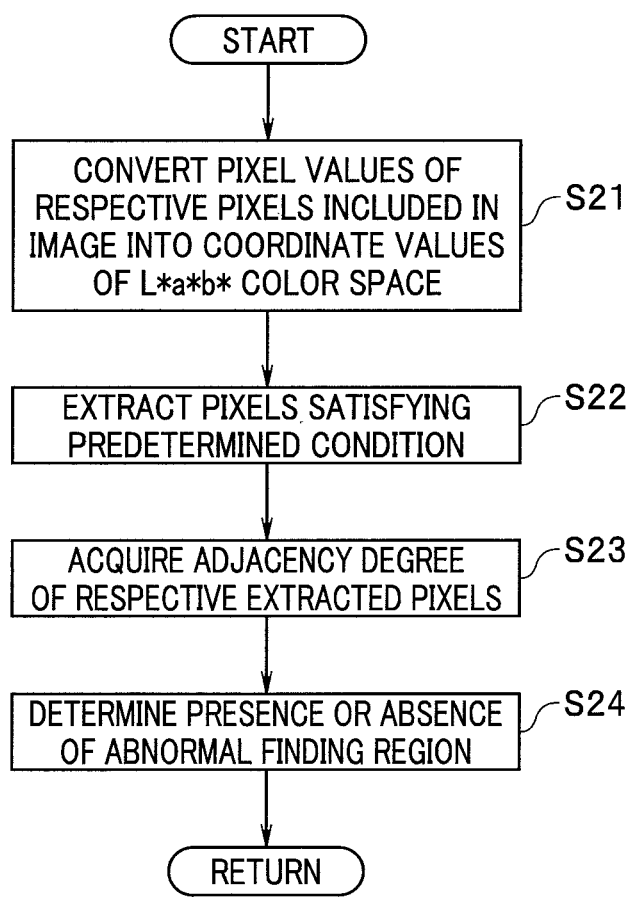
FIG. 6 is a flowchart for explaining a specific example of analysis processing performed in an endoscope system according to a second embodiment.

FIG. 6 relates to a second embodiment of the present invention.

Note that, in this embodiment, an overview of operation of the control section 44 is the same as the flowchart of FIG.

4. On the other hand, a part of details of the operation of the control section 44 is different from the details of the operation of the control section 44 in the first embodiment. Accordingly, in the following explanation, the overview of the operation of the control section 44 is explained with reference to the flowchart of FIG. 4. Differences of the details of the operation of the control section 44 from the details of the operation of the control section 44 in the first embodiment are intensively explained.

For example, when an instruction for starting observation by the endoscope 2 is performed according to the operation of the scope switch 23 by the user, the illumination-light setting section 44b sets, as the illumination light EL1, the V light, the G light, and the R light selected out of the light of the five colors emitted from the respective LEDs of the light emitting section 31 and outputs illumination light setting information ESC indicating setting content of the illumination light EL1 to the control-signal generating section 44c.

The control-signal generating section 44c generates, based on the illumination light setting information ESC outputted from the illumination-light setting section 44b, a control signal for causing the light-source control section 34 to generate the illumination light EL1 and outputs the control signal to the light-source control section 34. The control-signal generating section 44c generates, based on the illumination light setting information ESC outputted from the illumination-light setting section 44b, a control signal for causing the image processing section 42 to generate image data of respective color components corresponding to return light of the illumination light EL1 and outputs the control signal to the image processing section 42. The control-signal generating section 44c generates, based on the illumination light setting information ESC outputted from the illumination-light setting section 44b, in the irradiation period of the illumination light EL1, a control signal for causing the observation-image generating section 43 to stop generation of an observation image and causing the observation-image generating section 43 to hold the image date of the respective color components outputted from the image processing section 42 and outputs the control signal to the observation-image generating section 43.

According to the operations of the illumination-light setting section 44b and the control-signal generating section 44c explained above, the illumination light EL1 including the V light, the G light, and the R light is irradiated on an object including a biological tissue, an image pickup signal obtained by picking up an image of return light from the object is outputted from the image pickup section 21, and image data ID3 generated according to the image pickup signal is outputted from the signal processing section 41.

The image processing section 42 respectively generates, based on the image data ID3 outputted from the signal processing section 41 and a control signal outputted from the control-signal generating section 44c, in the irradiation period of the illumination light EL1, image data IDV3 of a violet component included in the image data ID3, image data IDG3 of a green component included in the image data ID3, and image data IDR3 of a red component included in the image data ID3, applies predetermined image processing to the generated image data, and outputs the respective image data to the observation-image generating section 43.

The observation-image generating section 43 holds, based on a control signal outputted from the control section 44, in the irradiation period of the illumination light ELL the image data (the image data IDV3, the image data IDG3, and the image data IDR3) of the respective color components outputted from the image processing section 42.

The image analyzing section 44a applies analysis processing to the image data ID3 equivalent to an image acquired during the irradiation of the illumination light EL1 and outputs, to the illumination-light setting section 44b, analysis result information ARC indicating an analysis result obtained by the analysis processing (step S1 in FIG. 4).

A specific example of the analysis processing performed by the image analyzing section 44a in this embodiment is explained below with reference to FIG. 6. FIG. 6 is a flowchart for explaining a specific example of analysis processing performed in an endoscope system according to the second embodiment.

The image analyzing section 44a performs processing for converting pixel values of RGB of respective pixels included in the image data ID3 outputted from the signal processing section 41 into coordinate values of an L*a*b* color space (step S21 in FIG. 6).

The image analyzing section 44a performs, based on the respective coordinate values obtained through the processing in step S21 in FIG. 6, processing for extracting pixels satisfying a predetermined condition out of the respective pixels included in the image data ID3 (step S22 in FIG. 6).

More specifically, the image analyzing section 44a performs, for example, processing for extracting, out of the respective pixels included in the image data ID3, pixels having an a* value smaller than an average of a* values of the respective pixels included in the image data ID3 and having a b* value larger than an average of b* values of the respective pixels included in the image data ID3.

Alternatively, for example, when a coordinate value (a*, b*) in the respective pixels included in the image data ID3 is represented by a coordinate value (r, θ) of a polar coordinate form and a coordinate value of the polar coordinate form obtained based on an average of the a* values and an average of b* values of the respective pixels included in the image data ID3 is represented by (rt, θt), the image analyzing section 44a performs processing for extracting pixels having an r value equal to or larger than a radius vector rt and having a θ value equal to or larger than an angle θt and equal to or smaller than 90 degrees.

The image analyzing section 44a performs processing for acquiring an adjacency degree AD of the respective extracted pixels equivalent to a value indicating an indicator of an adjacent state of the respective extracted pixels extracted by the processing in step S22 in FIG. 6 (step S23 in FIG. 6).

More specifically, for example, when one or more extracted pixels are present in eight vicinities of one pixel of attention selected out of the respective extracted pixels, the image analyzing section 44a acquires 1 as a count value corresponding to the one extracted pixel. For example, when other extracted pixels are absent in eight vicinities of one pixel of attention selected out of the respective extracted pixels, the image analyzing section 44a acquires 0 as a count value corresponding to the one extracted pixel. The image analyzing section 44a acquires, as the adjacency degree AD, a total of count values acquired in respective pixels of attention.

The image analyzing section 44a performs, based on the adjacency degree AD obtained through the processing in step S23 in FIG. 6, processing for judging presence or absence of an abnormal finding region in the image data ID3 that is a processing target in step S21 in FIG. 6 (step S24 in FIG. 6).

More specifically, for example, when the adjacency degree AD is equal to or larger than a threshold THC, the image analyzing section 44a acquires a judgement result indicating that an abnormal finding region is included in the image data ID3. For example, when the adjacency degree AD is smaller than the threshold THC, the image analyzing section 44a acquires a judgement result indicating that an abnormality finding region is not included in the image data ID3.

In other words, the image analyzing section 44a in this embodiment applies analysis processing indicated by the flowchart of FIG. 6 to the image data ID3 outputted from the signal processing section 41, acquires, as an analysis result of the analysis processing, a judgement result relating to presence or absence of an abnormal finding region in the image data ID3, and outputs the analysis result information ARC indicating the acquired analysis result to the illumination-light setting section 44b. The image analyzing section 44a in this embodiment analyzes the image data ID3 obtained by picking up an image of an object including a biological tissue during the irradiation of the illumination light EL1 to thereby acquire, as an analysis result relating to presence or absence of an abnormal finding in the image data ID3, a judgement result relating to whether an abnormal finding region having a predetermined color tone (a yellow tone) is included in the image data ID3.

Note that the image analyzing section 44a in this embodiment may acquire judgement result relating to presence or absence of an abnormal finding region in the image data ID3 by performing processing explained below instead of performing the processing in step S23 and step S24 in FIG. 6.

The image analyzing section 44a generates a connected region by connecting one pixel of attention selected out of the respective extracted pixels and pixels in eight vicinities of the one pixel of attention. Further, the image analyzing section 44a gives the same label to a plurality of connected regions in contact with or overlapping one another to thereby integrate the plurality of connected regions as one label region. When the number of label regions having the number of pixels equal to or larger than a predetermined number of pixels is equal to or larger than a predetermined number, the image analyzing section 44a acquires a judgement result indicating that an abnormal finding region is included in the image data ID3. When the number of label regions having the number of pixels equal to or larger than the predetermined number of pixels is smaller than the predetermined number, the image analyzing section 44a acquires a judgement result indicating that an abnormal finding region is not included in the image data ID3.

The illumination-light setting section 44b sets, based on the analysis result information ARC outputted from the image analyzing section 44a, as the illumination light EL2, light of one or more colors selected out of the light of the five colors emitted from the respective LEDs of the light emitting section 31 (step S2 in FIG. 4) and outputs illumination light setting information ESD indicating setting content of the illumination light EL2 to the control-signal generating section 44c.

More specifically, the illumination-light setting section 44b sets, based on the analysis result information ARC outputted from the image analyzing section 44a, for example, when it is detected that an abnormal finding region is included in the image data ID3, as the illumination light EL2, the V light and the A light selected out of the light of the five colors emitted from the respective LEDs of the light emitting section 31 and outputs, to the control-signal generating section 44c, the illumination light setting information ESD indicating the setting content of the illumination light EL2. The illumination-light setting section 44b sets, based on the analysis result information ARC outputted from the image analyzing section 44a, for example, when it is detected that an abnormal finding region is not included in the image data ID3, as the illumination light EL2, the B light and the A light selected out of the light of the five colors emitted from the respective LEDs of the light emitting section 31 and outputs, to the control-signal generating section 44c, the illumination light setting information ESD indicating the setting content of the illumination light EL2.

In other words, the illumination-light setting section 44b in this embodiment combines light in one or more wavelength bands selected out of the light of the five colors emitted from the respective LEDs of the light emitting section 31 and sets the light as the illumination light EL2 such that the illumination light EL2 has a different wavelength band according to the analysis result indicated by the analysis result information ARC outputted from the image analyzing section 44a.

The control-signal generating section 44c generates, based on the illumination light setting information ESD outputted from the illumination-light setting section 44b, a control signal for causing the light-source control section 34 to generate the illumination light EL2 and outputs the control signal to the light-source control section 34 (step S3 in FIG. 4). The control-signal generating section 44c generates, based on the illumination light setting information ESD outputted from the illumination-light setting section 44b, a control signal for causing the image processing section 42 to generate image data of respective color components corresponding to return light of the illumination light EL2 and outputs the control signal to the image processing section 42 (step S3 in FIG. 4). The control-signal generating section 44c generates, based on the illumination light setting information ESD outputted from the illumination-light setting section 44b, a control signal for causing the observation-image generating section 43 to generate an observation image using image data of one or more color components among image data of respective color components outputted from the image processing section 42 during the irradiation of the illumination light EL1 and image data of one or more color components among image data of respective color components outputted from the image processing section 42 during the irradiation of the illumination light EL2 and outputs the control signal to the observation-image generating section 43 (step S3 in FIG. 4).

According to the operations of the illumination-light setting section 44b and the control-signal generating section 44c explained above, for example, when an abnormal finding region is included in the image data ID3, the illumination light EL2 including the V light and the A light is irradiated on an object including a biological tissue, an image pickup signal obtained by picking up an image of return light from the object is outputted from the image pickup section 21, and image data ID4 generated according to the image pickup signal is outputted from the signal processing section 41. According to the operations of the illumination-light setting section 44b and the control-signal generating section 44c explained above, for example, when an abnormal finding region is not included in the image data ID3, the illumination light EL2 including the B light and the A light is irradiated on an object including a biological tissue, an image pickup signal obtained by picking up an image of return light from the object is outputted from the image pickup section 21, and image data ID2 generated according to the image pickup signal is outputted from the signal processing section 41.

The image processing section 42 respectively generates, based on the image data ID4 outputted from the signal processing section 41 and a control signal outputted from the control-signal generating section 44c, for example, when an abnormal finding region is included in the image data ID3, image data IDV4 of a violet component included in the image data ID4 and image data IDA4 of an amber component included in the image data ID4, applies predetermined image processing to the generated respective image data, and outputs the respective image data to the observation-image generating section 43. The image processing section 42 respectively generates, based on the image data ID4 outputted from the signal processing section 41 and a control signal outputted from the control-signal generating section 44c, for example, when an abnormal finding region is not included in the image data ID3, image data IDB4 of a blue component included in the image data ID4 and image data IDA4 of an amber component included in the image data ID4, applies predetermined image processing to the generated respective image data, and outputs the respective image data to the observation-image generating section 43.

Based on a control signal outputted from the control section 44, for example, when an abnormal finding region is included in the image data ID3, the observation-image generating section 43 allocates image data obtained by adding up, for each of pixels, the image data IDV3 and IDV4 aligned with each other to the B channel of the display apparatus 5, allocates the image data IDG3 to the G channel of the display apparatus 5, and allocates the image data IDA4 to the R channel of the display apparatus 5 to thereby generate an observation image KGD and outputs the generated observation image KGD to the display apparatus 5. Based on a control signal outputted from the control section 44, for example, when an abnormal finding region is not included in the image data ID3, the observation-image generating section 43 allocates image data obtained by adding up, for each of pixels, the image data IDV3 and IDB4 aligned with each other to the B channel of the display apparatus 5, allocates the image data IDG3 to the G channel of the display apparatus 5, and allocates image data obtained by adding up, for each of pixels, the image data IDR3 and IDA4 aligned with each other to the R channel of the display apparatus 5 to thereby generate an observation image KGE and outputs the generated observation image KGE to the display apparatus 5.

After outputting the illumination light setting information ESD obtained through the processing in step S2 in FIG. 4 to the control-signal generating section 44c, the illumination-light setting section 44b outputs the illumination light setting information ESC to the control-signal generating section 44c again.

The control-signal generating section 44c generates, based on the illumination light setting information ESC outputted from the illumination-light setting section 44b, a control signal for causing the light-source control section 34 to generate the illumination light EL1 and outputs the control signal to the light-source control section 34. The control-signal generating section 44c generates, based on the illumination light setting information ESC outputted from the illumination-light setting section 44b, a control signal for causing the image processing section 42 to generate image data of respective color components corresponding to return light of the illumination light EL1 and outputs the control signal to the image processing section 42. The control-signal generating section 44c generates, based on the illumination light setting information ESC outputted from the illumination-light setting section 44b, in the irradiation period of the illumination light EL1, a control signal for causing the observation-image generating section 43 to stop generation of an observation image and causing the observation-image generating section 43 to hold image data of respective color components outputted from the image processing section 42 and outputs the control signal to the observation-image generating section 43.

The image analyzing section 44a applies analysis processing by the same method as step S1 in FIG. 4 to the image data ID3 equivalent to an image acquired during the irradiation of the illumination light EL1 and outputs, to the illumination-light setting section 44b, analysis result information ARD indicating an analysis result obtained by the analysis processing (step S4 in FIG. 4).

The illumination-light setting section 44b performs processing for judging whether an analysis result indicated by latest analysis result information ARDN equivalent to the analysis result information ARD obtained through the processing in step S4 in FIG. 4 is the same as an analysis result indicated by analysis result information ARDP in the past equivalent to the analysis result information ARC or ARD referred to when the present illumination light EL2 is set (step S5 in FIG. 4).

When acquiring a judgement result indicating that the analysis result indicated by the latest analysis result information ARDN is the same as the analysis result indicated by the analysis result information ARDP in the past (S5: YES), the illumination-light setting section 44b continues to perform processing in step S6 in FIG. 4 explained below. When acquiring a judgement result indicating that the analysis result indicated by the latest analysis result information ARDN is different from the analysis result indicated by the analysis result information ARDP in the past (S5: NO), the illumination-light setting section 44b continues to perform processing in step S7 in FIG. 4 explained below.

In order to maintain present setting content of the illumination light EL2, the illumination-light setting section 44b outputs, to the control-signal generating section 44c, the illumination light setting information ESD indicating the same setting content as the present setting content (step S6 in FIG. 4).

The illumination-light setting section 44b performs processing for judging whether the number of times the same analysis result as the analysis result indicated by the latest analysis result information ARDN is continuously acquired is equal to or more than a predetermined number of times (step S7 in FIG. 4).

When acquiring a judgement result indicating that the number of times the same analysis result as the analysis result indicated by the latest analysis result information ARDN is continuously acquired is less than the predetermined number of times (S7: NO), the illumination-light setting section 44b continues to perform the processing in step S6 in FIG. 4. When acquiring a judgement result indicating that the number of times the same analysis result as the analysis result indicated by the latest analysis result information ARDN is continuously acquired is equal to or more than the predetermined number of times (S7: YES), the illumination-light setting section 44b changes the setting content of the illumination light EL2 to setting content corresponding to the analysis result indicated by the latest analysis result information ARDN and outputs the illumination light setting information ESD indicating the setting content of the illumination light EL2 after the change to the control-signal generating section 44c (step S8 in FIG. 4).

The control-signal generating section 44c generates, based on the illumination light setting information ESD obtained through the processing in step S6 or step S8 in FIG. 4, a control signal for causing the light-source control section 34 to generate the illumination light EL2 corresponding to the illumination light setting information ESD and outputs the control signal to the light-source control section 34 (step S9 in FIG. 4). The control-signal generating section 44c generates, based on the illumination light setting information ESD obtained through the processing in step S6 or step S8 in FIG. 4, control signals for causing the image processing section 42 and the observation-image generating section 43 to perform operation (relating to generation of an observation image) corresponding to the illumination light setting information ESD and outputs the control signals respectively to the image processing section 42 and the observation-image generating section 43 (step S9 in FIG. 4).

According to this embodiment, for example, according to the operation of the scope switch 23 by the user, the processing in step S4 to step S9 in FIG. 4 is repeatedly performed until an instruction to end the observation by the endoscope 2 is performed. According to this embodiment, a spectrum of the illumination light EL2 is set according to presence or absence of an abnormal finding region in the image data ID3 obtained when the illumination light EL1 set to a predetermined spectrum is irradiated on an object. An observation image corresponding to the illumination light EL2 is displayed on the display apparatus 5. According to this embodiment, for example, when an abnormal finding region ABB visualized as a reddened region during white light observation and visualized as brownish area during narrowband light observation is included in the image data ID3, the observation image KGD in which the abnormal finding region ABB is highlighted in yellow is displayed on the display apparatus 5 (as an observation image corresponding to the illumination light EL2). Therefore, it is possible to improve visibility of the abnormal finding region ABB. According to this embodiment, for example, when the abnormal finding region ABB is included in the image data ID3, as the illumination light EL2 including the A light is irradiated on the abnormal finding region ABB, the observation image KGD in which a state of a mucous membrane deep layer in the abnormal finding region ABB is visible is displayed on the display apparatus 5 (as an observation image corresponding to the illumination light EL2). Therefore, it is possible to confirm, at a time, changes in states of a mucous membrane from a surface layer to a deep layer of the abnormal finding region ABB. Therefore, according to this embodiment, it is possible to reduce a burden on a surgeon who performs work relating to diagnosis of an abnormal finding.

Note that, in this embodiment, for example, when an abnormal finding region is included in the image data ID3, the illumination-light setting section 44b may set, as the illumination light EL2, the V light selected out of the light of the five colors emitted from the respective LEDs of the light emitting section 31. In such a case, for example, the observation-image generating section 43 may allocate image data obtained by adding up, for each of pixels, the image data IDV3 and IDV4 aligned with each other respectively to the B channel and the G channel of the display apparatus 5 and allocate the image data IDG3 to the R channel of the display apparatus 5 to thereby generate an observation image KGF. With such a configuration, when the abnormal finding region ABB is included in the image data ID3, the abnormal finding region ABB is highlighted in a dark reddish brown according to the allocation of the image data. The observation image KGF, brightness of an image entire region of which including the abnormal finding region ABB is improved according to the addition of the image data IDV3 and IDV4, is displayed on the display apparatus 5 (as an observation image corresponding to the illumination light EL2). Therefore, it is possible to improve visibility of the abnormal finding region ABB.

Third Embodiment

Figure 7:
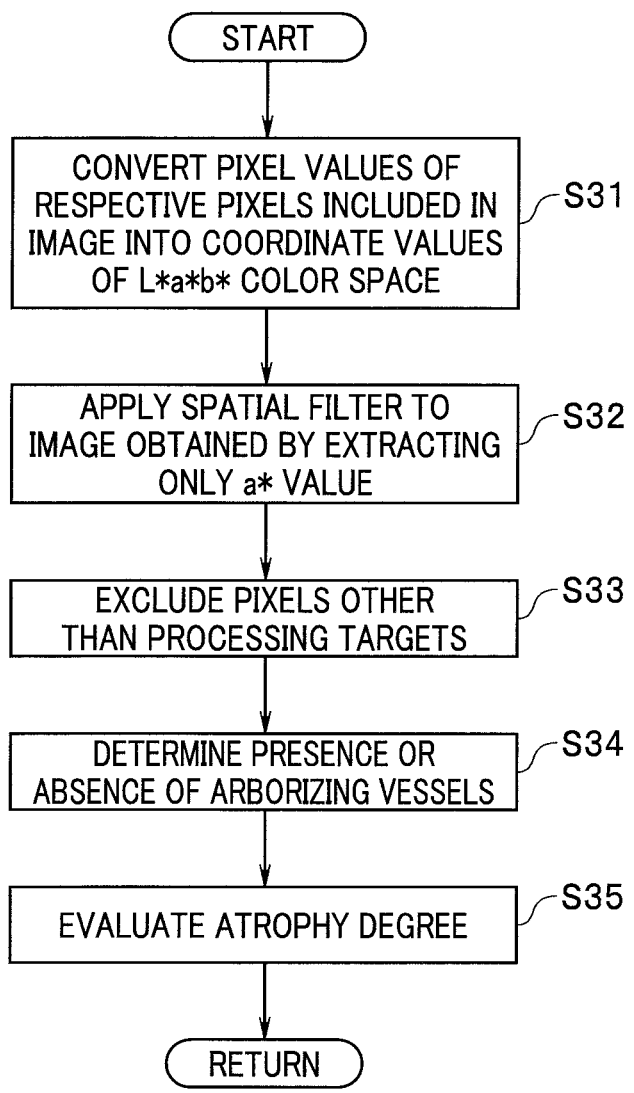
FIG. 7 is a flowchart for explaining a specific example of analysis processing performed in an endoscope system according to a third embodiment.
Figure 8:
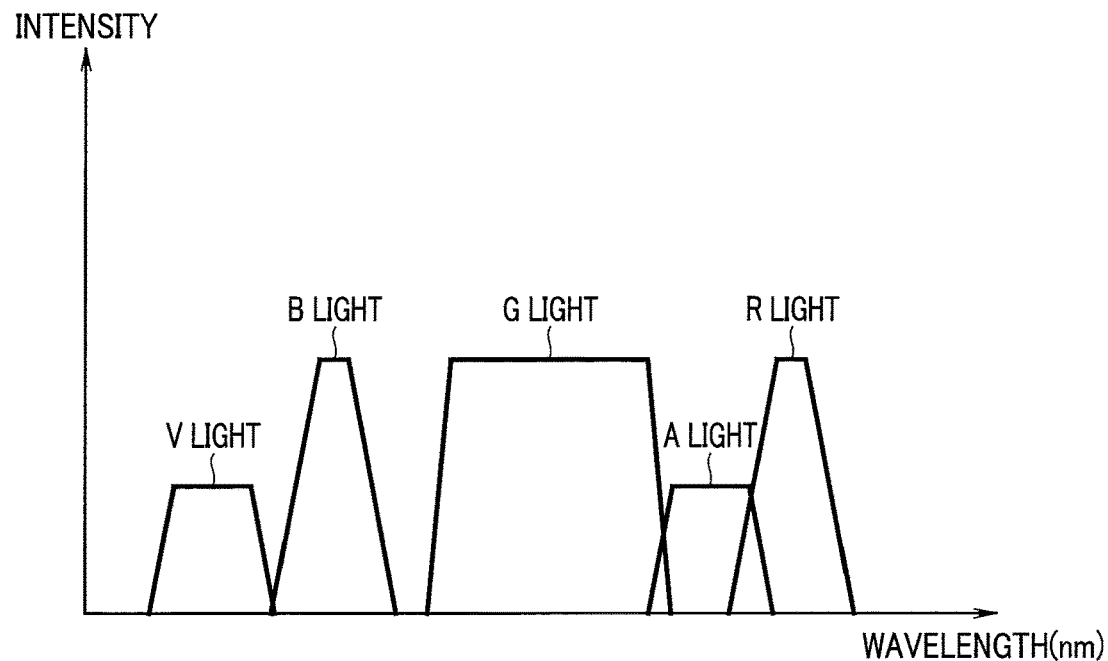
FIG. 8 is a diagram showing an example of illumination light emitted from a light source apparatus of an endoscope system according to a modification of the third embodiment.
Figure 9:
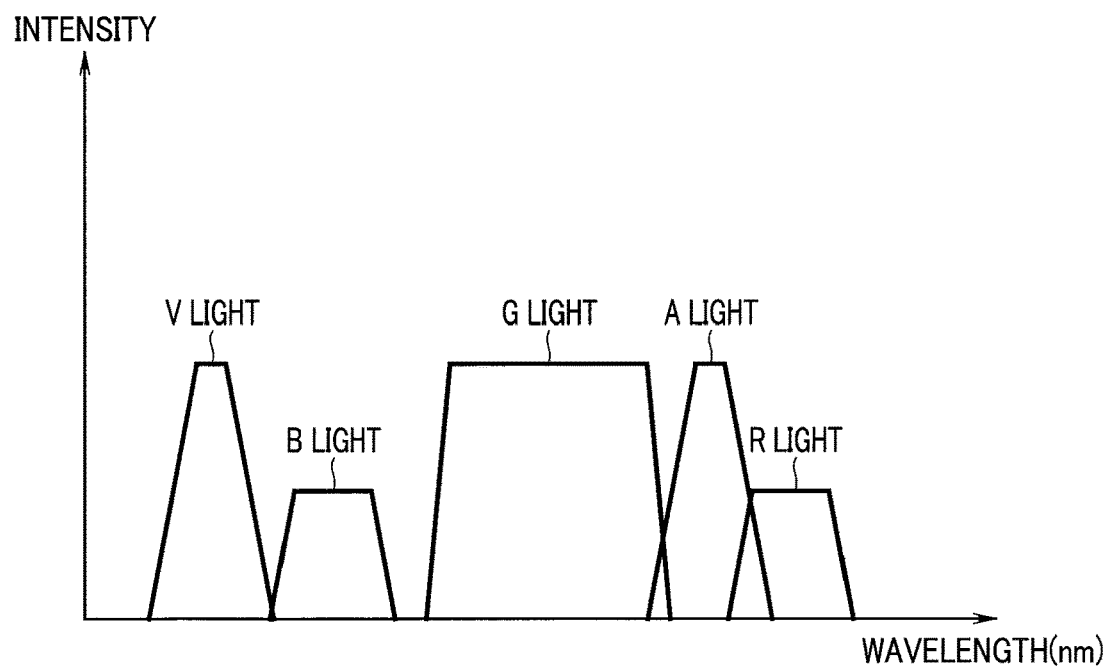
FIG. 9 is a diagram showing an example of illumination light emitted from the light source apparatus of the endoscope system according to the modification of the third embodiment.

FIG. 7 to FIG. 9 relate to a third embodiment of the present invention.

Note that, in this embodiment, an overview of operation of the control section 44 is the same as the flowchart of FIG. 4. On the other hand, a part of details of the operation of the control section 44 is different from the details of the operation of the control section 44 in the first embodiment. Accordingly, in the following explanation, the overview of the operation of the control section 44 is explained with reference to the flowchart of FIG. 4. Differences of the details of the operation of the control section 44 from the details of the operation of the control section 44 in both of the first embodiment and the second embodiment are intensively explained. In this embodiment, for example, the following explanation is based on a premise that the control section 44 detects, based on endoscope information stored in the scope memory 24, that the endoscope 2 corresponds to a model for an upper digestive tract such as stomach. In this embodiment, in the following explanation, as an example, an image of an object present inside the stomach is picked up and the object is observed.

For example, when an instruction for starting observation by the endoscope 2 is performed according to operation of the scope switch 23 by the user, the illumination-light setting section 44b sets, as the illumination light EL1, the V light, the G light, and the R light selected out of the light of the five colors emitted from the respective LEDs of the light emitting section 31 and outputs illumination light setting information ESE indicating setting content of the illumination light EL1 to the control-signal generating section 44c.

The control-signal generating section 44c generates, based on the illumination light setting information ESE outputted from the illumination-light setting section 44b, a control signal for causing the light-source control section 34 to generate the illumination light EL1 and outputs the control signal to the light-source control section 34. The control-signal generating section 44c generates, based on the illumination light setting information ESE outputted from the illumination-light setting section 44b, a control signal for causing the image processing section 42 to generate image data of respective color components corresponding to return light of the illumination light EL1 and outputs the control signal to the image processing section 42. The control-signal generating section 44c generates, based on the illumination light setting information ESE outputted from the illumination-light setting section 44b, in the irradiation period of the illumination light EL1, a control signal for causing the observation-image generating section 43 to stop generation of an observation image and causing the observation-image generating section 43 to hold image data of respective color components outputted from the image processing section 42 and outputs the control signal to the observation-image generating section 43.

According to the operations of the illumination-light setting section 44b and the control-signal generating section 44c explained above, the illumination light EL1 including the V light, the G light, and the R light is irradiated on an object including a biological tissue, an image pickup signal obtained by picking up an image of return light from the object is outputted from the image pickup section 21, and image data ID5 generated according to the image pickup signal is outputted from the signal processing section 41.

The image processing section 42 respectively generates, based on the image data ID5 outputted from the signal processing section 41 and a control signal outputted from the control-signal generating section 44*c*, in the irradiation period of the illumination light EL1, image data IDV5 of a violet component included in the image data ID5, image data IDG5 of a green component included in the image data ID5, and image data IDR5 of a red component included in the image data ID5, applies predetermined image processing to the generated respective image data, and outputs the respective image data to the observation-image generating section 43.

The observation-image generating section 43 holds, based on a control signal outputted from the control section 44, in the irradiation period of the illumination light EL1, the image data (the image data IDV5, the image data IDG5, and the image data IDR5) of the respective color components outputted from the image processing section 42.

The image analyzing section 44*a* applies analysis processing to the image data ID5 equivalent to an image acquired during the irradiation of the illumination light EL1 and outputs analysis result information ARE indicating an analysis result obtained by the analysis processing to the illumination-light setting section 44*b* (step S1 in FIG. 4).

A specific example of the analysis processing performed by the image analyzing section 44*a* in this embodiment is explained below with reference to FIG. 7. FIG. 7 is a flowchart for explaining a specific example of analysis processing performed in an endoscope system according to the third embodiment.

The image analyzing section 44*a* performs processing for converting pixel values of RGB of respective pixels included in the image data ID5 outputted from the signal processing section 41 into coordinate values of an L*a*b* color space (step S31 in FIG. 7).

The image analyzing section 44*a* performs, based on the respective coordinate values obtained through the processing in step S31 of FIG. 7, processing for generating image data ID5*a*, which is obtained by extracting only a* values of the respective pixels of the image data ID5, and applying a spatial filter SFA having a predetermined bandpass characteristic to the generated image data ID5*a* (step S32 in FIG. 7).

The image analyzing section 44*a* performs, based on the respective coordinate values obtained through the processing in step S31 in FIG. 7, processing for excluding pixels other than processing targets from the respective pixels included in the image data ID5 (step S33 in FIG. 7).

More specifically, the image analyzing section 44*a* extracts, for example, out of the respective pixels included in the image data ID5, pixels in which halation occurs equivalent to pixels satisfying conditions that an L* value obtained by the processing in step S31 in FIG. 7 is equal to or larger than a threshold THD and both of an absolute value of an a* value and an absolute value of a b* value obtained by the processing in step S31 in FIG. 7 belong to a predetermined range and excludes the extracted pixels as the pixels other than the processing targets.

The image analyzing section 44*a* performs, based on a* values in pixels not excluded as the pixels other than the processing targets by the processing in step S33 in FIG. 7 among the respective pixels included in image data ID5*b* equivalent to a processing result obtained through the processing in step S32 in FIG. 7, processing for judging presence or absence of arborizing vessels in the image data ID5 (step S34 in FIG. 7).

More specifically, for example, when the number of pixels having a* values larger than 0 is equal to or larger than a threshold THE, the image analyzing section 44*a* acquires a judgement result indicating that arborizing vessels are included in the image data ID5. For example, when the number of pixels having a* values larger than 0 is smaller than the threshold THE, the image analyzing section 44*a* acquires a judgement result indicating that arborizing vessels are not included in the image data ID5.

The image analyzing section 44*a* performs, based on the judgement result relating to presence or absence of arborizing vessels obtained through the processing in step S33 in FIG. 7, processing for evaluating an atrophy degree of a gastric mucosa included in the image data ID5 (step S35 in FIG. 7).

More specifically, for example, when the judgement result indicating that arborizing vessels are not included in the image data ID5 is obtained, the image analyzing section 44*a* obtains an evaluation result indicating that the atrophy degree of the gastric mucosa included in the image data ID5 is a low degree or a medium degree. For example, when the judgement result indicating that arborizing vessels are included in the image data ID5 is obtained, the image analyzing section 44*a* obtains an evaluation result indicating that the atrophy degree of the gastric mucosa included in the image data ID5 is a high degree.

In other words, the image analyzing section 44*a* in this embodiment applies the analysis processing shown in the flowchart of FIG. 7 to the image data ID5 outputted from the signal processing section 41, acquires, as an analysis result of the analysis processing, an evaluation result relating to an atrophy degree of a gastric mucosa included in the image data ID5, and outputs the analysis result information ARE indicating the acquired analysis result to the illumination-light setting section 44*b*. The image analyzing section 44*a* in this embodiment analyzes the image data ID5 obtained by picking up an image of an object including a biological tissue during the irradiation of the illumination light EL1 to thereby obtain, as an analysis result relating to presence or absence of an abnormal finding in the image data ID5, the evaluation result relating to the atrophy degree of the mucosa included in the image data ID5.

Note that the image analyzing section 44*a* in this embodiment may perform, based on an evaluation result of a color tone of the image data ID5 obtained by performing the same processing as the processing in step S11 to step S14 in FIG. 5 and the judgement result obtained through the processing in step S33 in FIG. 7, processing for evaluating the atrophy degree of the gastric mucosa included in the image data ID5. In such a case, for example, when the color tone of the image data ID5 is equivalent to a color tone of a discolored mucosa and arborizing vessels are included in the image data ID5, it is possible to obtain an evaluation result indicating that the atrophy degree of the gastric mucosa included in the image data ID5 is the high degree.

The image analyzing section 44*a* in this embodiment may read, for example, in step S34 in FIG. 7, test information of endoscopy in the past from a database storing electronic medical records and the like and perform, based on information concerning gastritis included in the read test information and the judgement result obtained through the processing in step S33 in FIG. 7, processing for evaluating the atrophy degree of the gastric mucosa included in the image data ID5. Note that, as the information concerning gastritis, for example, information indicating the atrophy degree of the gastric mucosa, information indicating presence or absence of infection of Helicobacter pylori, and information indicating presence or absence of disinfection of Helicobacter pylori can be used.

The illumination-light setting section 44b sets, based on the analysis result information ARE outputted from the image analyzing section 44a, as the illumination light EL2, light of one or more colors selected out of the light of the five colors emitted from the respective LEDs of the light emitting section 31 (step S2 in FIG. 4) and outputs illumination light setting information ESF indicating setting content of the illumination light EL2 to the control-signal generating section 44c.

More specifically, for example, when detecting, based on the analysis result information ARE outputted from the image analyzing section 44a, that the atrophy degree of the gastric mucosa included in the image data ID5 is the low degree or the medium degree, the illumination-light setting section 44b sets, as the illumination light EL2, the V light, the G light, and the A light selected out of the light of the five colors emitted from the respective LEDs of the light emitting section 31 and outputs the illumination light setting information ESF indicating the setting content of the illumination light EL2 to the control-signal generating section 44c. When detecting, based on the analysis result information ARC outputted from the image analyzing section 44a, that the atrophy degree of the gastric mucosa included in the image data ID5 is the high degree, the illumination-light setting section 44b sets, as the illumination light EL2, the B light, the G light, and the A light selected out of the light of the five colors emitted from the respective LEDs of the light emitting section 31 and outputs the illumination light setting information ESD indicating the setting content of the illumination light EL2 to the control-signal generating section 44c.

In other words, the illumination-light setting section 44b in this embodiment combines light in one or more wavelength bands selected out of the light of the five colors emitted from the respective LEDs of the light emitting section 31 and sets the light as the illumination light EL2 such that the illumination light EL2 has a different wavelength band according to an analysis result indicated by the analysis result information ARE outputted from the image analyzing section 44a.

The control-signal generating section 44c generates, based on the illumination light setting information ESF outputted from the illumination-light setting section 44b, a control signal for causing the light-source control section 34 to generate the illumination light EL2 and outputs the control signal to the light-source control section 34 (step S3 in FIG. 4). The control-signal generating section 44c generates, based on the illumination light setting information ESF outputted from the illumination-light setting section 44b, a control signal for causing the image processing section 42 to generate image data of respective color components corresponding to return light of the illumination light EL2 and outputs the control signal to the image processing section 42 (step S3 in FIG. 4). The control-signal generating section 44c generates, based on the illumination light setting information ESF outputted from the illumination-light setting section 44b, a control signal for causing the observation-image generating section 43 to generate an observation image using at least image data of respective color components outputted from the image processing section 42 during the irradiation of the illumination light EL2 and outputs the control signal to the observation-image generating section 43 (step S3 in FIG. 4).

According to the operations of the illumination-light setting section 44b and the control-signal generating section 44c explained above, for example, when the atrophy degree of the gastric mucosa included in the image data ID5 is the low degree or the medium degree, the illumination light EL2 including the V light, the G light, and the A light is irradiated on an object including a biological tissue, an image pickup signal obtained by picking up an image of return light from the object is outputted from the image pickup section 21, and image data ID6 generated according to the image pickup signal is outputted from the signal processing section 41. According to the operations of the illumination-light setting section 44b and the control-signal generating section 44c explained above, for example, when the atrophy degree of the gastric mucosa included in the image data ID5 is the high degree, the illumination light EL2 including the B light, the G light, and the A light is irradiated on an object including a biological tissue, an image pickup signal obtained by picking up an image of return light from the object is outputted from the image pickup section 21, and the image data ID6 generated according to the image pickup signal is outputted from the signal processing section 41.

The image processing section 42 respectively generates, based on the image data ID6 outputted from the signal processing section 41 and a control signal outputted from the control-signal generating section 44c, for example, when the atrophy degree of the gastric mucosa included in the image data ID5 is the low degree or the medium degree, image data IDV6 of a violet component included in the image data ID6, image data IDG6 of a green component included in the image data ID6, and image data IDA6 of an amber component included in the image data ID6, applies predetermined image processing to the generated respective image data, and outputs the image data to the observation-image generating section 43. The image processing section 42 respectively generates, based on the image data ID6 outputted from the signal processing section 41 and a control signal outputted from the control-signal generating section 44c, for example, when the atrophy degree of the gastric mucosa included in the image data ID5 is the high degree, image data IDB6 of a blue component included in the image data ID6, image data IDG6 of a green component included in the image data ID6, and image data IDA6 of an amber component included in the image data ID6, applies predetermined image processing to the generated respective image data, and outputs the image data to the observation-image generating section 43.

Note that, in this embodiment, for example, when the atrophy degree of the gastric mucosa included in the image data ID5 is the low degree or the medium degree, the image processing section 42 may apply, to at least one image data among the image data IDV6, IDG6, and IDA6, structure highlighting processing or gradation conversion processing for showing up unevenness of the gastric mucosa.

Based on a control signal outputted from the control section 44, for example, when the atrophy degree of the gastric mucosa included in the image data ID5 is the low degree or the medium degree, the observation-image generating section 43 allocates the image data IDV6 to the B channel of the display apparatus 5, allocates the image data IDG6 to the G channel of the display apparatus 5, and allocates the image data IDA6 to the R channel of the display apparatus 5 to thereby generate an observation image KGG and outputs the generated observation image KGG to the display apparatus 5. Based on a control signal outputted from the control section 44, for example, when the atrophy degree of the gastric mucosa included in the image data ID5 is the high degree, the observation-image generating section 43 allocates image data obtained by adding up, for each of pixels, the image data IDV5 and IDB6 aligned with each other to the B channel of the display apparatus 5, allocates the image data IDG6 to the G channel of the display apparatus 5, and allocates image data obtained by adding up, for each of pixels, the image data IDR5 and IDA6 aligned with each other to the R channel of the display apparatus 5 to thereby generate an observation image KGH and outputs the generated observation image KGH to the display apparatus 5.

After outputting the illumination light setting information ESF obtained through the processing in step S2 in FIG. 4 to the control-signal generating section 44c, the illumination-light setting section 44b outputs the illumination light setting information ESE to the control-signal generating section 44c again.

The control-signal generating section 44c generates, based on the illumination light setting information ESE outputted from the illumination-light setting section 44b, a control signal for causing the light-source control section 34 to generate the illumination light EL1 and outputs the control signal to the light-source control section 34. The control-signal generating section 44c generates, based on the illumination light setting information ESE outputted from the illumination-light setting section 44b, a control signal for causing the image processing section 42 to generate image data of respective color components corresponding to return light of the illumination light EL1 and outputs the control signal to the image processing section 42. The control-signal generating section 44c generates, based on the illumination light setting information ESE outputted from the illumination-light setting section 44b, in the irradiation period of the illumination light EL1, a control signal for causing the observation-image generating section 43 to stop generation of an observation image and causing the observation-image generating section 43 to hold image data of respective color components outputted from the image processing section 42 and outputs the control signal to the observation-image generating section 43.

The image analyzing section 44a applies analysis processing by the same method as step S1 in FIG. 4 to the image data ID5 equivalent to an image acquired during the irradiation of the illumination light EL1 and outputs, to the illumination-light setting section 44b, analysis result information ARF indicating an analysis result obtained by the analysis processing (step S4 in FIG. 4).

The illumination-light setting section 44b performs processing for judging whether an analysis result indicated by latest analysis result information ARFN equivalent to the analysis result information ARF obtained through the processing in step S4 in FIG. 4 is the same as an analysis result indicated by analysis result information ARFP in the past equivalent to the analysis result information ARE or ARF referred to when the present illumination light EL2 is set (step S5 in FIG. 4).

When acquiring a judgement result indicating that the analysis result indicated by the latest analysis result information ARFP is the same as the analysis result indicated by the analysis result information ARFP in the past (S5: YES), the illumination-light setting section 44b continues to perform processing in step S6 in FIG. 4 explained below. When acquiring a judgement result indicating that the analysis result indicated by the latest analysis result information ARFN is different from the analysis result indicated by the analysis result information ARFP in the past (S5: NO), the illumination-light setting section 44b continues to perform processing in step S7 in FIG. 4 explained below.

In order to maintain present setting content of the illumination light EL2, the illumination-light setting section 44b outputs, to the control-signal generating section 44c, the illumination light setting information ESF indicating the same setting content as the present setting content (step S6 in FIG. 4).

The illumination-light setting section 44b performs processing for judging whether the number of times the same analysis result as the analysis result indicated by the latest analysis result information ARFN is continuously acquired is equal to or more than a predetermined number of times (step S7 in FIG. 4).

When acquiring a judgement result indicating that the number of times the same analysis result as the analysis result indicated by the latest analysis result information ARFN is continuously acquired is less than the predetermined number of times (S7: NO), the illumination-light setting section 44b continues to perform the processing in step S6 in FIG. 4. When acquiring a judgement result indicating that the number of times the same analysis result as the analysis result indicated by the latest analysis result information ARFN is continuously acquired is equal to or more than the predetermined number of times (S7: YES), the illumination-light setting section 44b changes the setting content of the illumination light EL2 to setting content corresponding to the analysis result indicated by the latest analysis result information ARFN and outputs the illumination light setting information ESF indicating the setting content of the illumination light EL2 after the change to the control-signal generating section 44c (step S8 in FIG. 4).

The control-signal generating section 44c generates, based on the illumination light setting information ESF obtained through the processing in step S6 or step S8 in FIG. 4, a control signal for causing the light-source control section 34 to generate the illumination light EL2 corresponding to the illumination light setting information ESF and outputs the control signal to the light-source control section 34 (step S9 in FIG. 4). The control-signal generating section 44c generates, based on the illumination light setting information ESF obtained through the processing in step S6 or step S8 in FIG. 4, control signals for causing the image processing section 42 and the observation-image generating section 43 to perform operation corresponding to the illumination light setting information ESF and outputs the control signals respectively to the image processing section 42 and the observation-image generating section 43 (step S9 in FIG. 4).

According to this embodiment, for example, according to the operation of the scope switch 23 by the user, the processing in step S4 to step S9 in FIG. 4 is repeatedly performed until an instruction to end the observation by the endoscope 2 is performed. According to this embodiment, a spectrum of the illumination light EL2 is set according to the atrophy degree of the gastric mucosa included in the image data ID5 obtained when the illumination light EL1 set to a predetermined spectrum is irradiated on an object. An observation image corresponding to the illumination light EL2 is displayed on the display apparatus 5. According to this embodiment, for example, when an abnormal finding region ABT equivalent to the gastric mucosa in which the atrophy of the low degree or the medium degree occurs is included in the image data ID5, the observation image KGG generated using the image data IDA6 corresponding to return light of the A light having an absorption coefficient to hemoglobin higher than an absorption coefficient of the R light is displayed on the display apparatus 5 (as an observation image corresponding to the illumination light EL2). Therefore, it is possible to improve visibility of reddening indicating a lesion of a gastritis similar type that occurs at a high frequency in the abnormal finding region ABT. According to this embodiment, for example, when the abnormal finding region ABT is included in the image data ID5, the observation image KGG generated using the image data IDA6 corresponding to return light of the A light is displayed on the display apparatus 5 (as an observation image corresponding to the illumination light EL2). Therefore, it is possible to confirm a histologic change of a mucosa deep layer in the abnormal finding region ABT. Therefore, according to this embodiment, it is possible to reduce a burden on a surgeon who performs work relating to diagnosis of an abnormal finding.

Note that, in this embodiment, for example, instead of the green LED 31c, an LED 31ga (not illustrated) that generates GS light, a center wavelength of which is set on a short wavelength side of a green region, and an LED 31gb (not illustrated) that generates GL light, a center wavelength of which is set on a long wavelength side of the green region, may be provided in the light emitting section 31. In such a configuration, the illumination light EL1 including the V light, the GS light, the GL light, and the R light only has to be irradiated on an object including a biological tissue. In the configuration explained above, when the atrophy degree of the gastric mucosa is the low degree or the medium degree, light including the GL light instead of the G light only has to be irradiated on the object as the illumination light EL2 and an observation image obtained by allocating image data IDGL of a green component corresponding to the GL light included in return light of the illumination light EL2 to the G channel of the display apparatus 5 only has to be displayed on the display apparatus 5. In the configuration explained above, when the atrophy degree of the gastric mucosa is the high degree, the illumination light EL2 including the GS light and the GL light instead of the G light only has to be irradiated on an object including a biological tissue and an observation image obtained by allocating image data IDGS of a green component corresponding to the GS light included in return light of the illumination light EL2 and image data IDGL of a green component corresponding to the GL light included in the return light of the illumination light EL2 to the G channel of the display apparatus 5 only has to be displayed on the display apparatus 5. With the configuration explained above, the GL light, a band width of which is narrower than a band width of the G light and the center wavelength of which is set on the long wavelength side of the green region, is irradiated on an object including a biological tissue. Therefore, for example, it is possible to cause the display apparatus 5 to display an observation image in which visibility of a mucosa deep layer is improved compared with an observation image displayed on the display apparatus 5 when the G light is irradiated on the object.

According to this embodiment, the illumination-light setting section 44b is not limited to selecting, when performing setting of illumination light, light of one or more colors out of the light of the five colors emitted from the respective LEDs of the light emitting section 31 and, for example, may change a light amount ratio in a state in which the light of the five colors are selected.

More specifically, for example, as shown in FIG. 8, in a state in which the V light, the B light, the G light, the A light, and the R light are selected as the illumination light EL1, the illumination-light setting section 44b may output illumination light setting information ESG indicating setting content of a light amount ratio ERG for setting a ratio of the V light included in the illumination light EL1 smaller than a ratio of the B light and setting a ratio of the A light included in the illumination light EL1 smaller than a ratio of the R light. For example, when the atrophy degree of the gastric mucosa is the low degree or the medium degree, as shown in FIG. 9, in a state in which the V light, the B light, the G light, the A light, and the R light are selected as the illumination light EL2, the illumination-light setting section 44b may output illumination light setting information ESH indicating setting content of a light amount ratio ERH for setting a ratio of the B light included in the illumination light EL2 smaller than a ratio of the V light and setting a ratio of the R light included in the illumination light EL2 smaller than a ratio of the A light. For example, when the atrophy degree of the gastric mucosa is the high degree, in a state in which the V light, the B light, the G light, the A light, and the R light are selected as the illumination light EL2, the illumination-light setting section 44b may output illumination light setting information ESI having the same setting content as the setting content of the illumination light setting information ESG explained above. Note that when the illumination light setting information ESG, ESH, and ESI explained above are outputted from the illumination-light setting section 44b, for example, a control signal for causing the observation-image generating section 43 to generate an observation image using image data outputted from the image processing section 42 during the irradiation of the illumination light EL2 only has to be outputted from the control-signal generating section 44c. FIG. 8 and FIG. 9 are diagrams showing an example of illumination light emitted from a light source apparatus of an endoscope system according to a modification of the third embodiment.

In other words, with the configuration explained above, when performing setting of illumination light, the illumination-light setting section 44b is not limited to performing setting for selectively causing the respective LEDs of the light emitting section 31 to emit light or turn off light. For example, the illumination-light setting section 44b causes the respective LEDs of the light emitting section 31 to emit light and, at the same time, performs setting for selectively changing a ratio of a light emission amount. With the configuration explained above, the illumination-light setting section 44b sets a light amount ratio of the light of the respective colors included in the illumination light EL1 to a light amount ratio ERM and sets a light amount ratio of the light of the respective colors included in the illumination light EL2 to a light amount ratio ERM or ERN, which is a light amount ratio that is different according to an evaluation result relating to the atrophy degree of the mucosa included in the image data ID5.

The configurations of the sections in this embodiment may be modified as appropriate to be applied to, for example, a case in which an image of an object present inside a large intestine is picked up and the object is observed. In such a case, the processing of the flowchart of FIG. 7 only has to be changed as appropriate to enable an evaluation result to be obtained by evaluating a state of an intestinal mucosa included in the image data ID5 according to an endoscopic finding classification such as a Matts classification.

The present invention is not limited to the respective embodiments explained above. It goes without saying that various changes and applications are possible within a range not departing from the gist of the invention.

What is claimed is:

1. An endoscope system comprising:
a light source apparatus configured to be able to emit light in a plurality of wavelength bands to irradiate an object with illumination light;
an image sensor configured to pick up an image of return light from the object on which the illumination light is irradiated; and
one or more processors, each comprising hardware, the one or more processors being configured to:
set, as illumination light for illuminating the object including a biological tissue present in a subject, first illumination light obtained by combining light in one or more wavelength bands selected out of the light in the plurality of wavelength bands and second illumination light obtained by combining light in one or more wavelength bands different from the first illumination light, selected out of the light in the plurality of wavelength bands;
control the light source apparatus to alternately irradiate, from the light source apparatus, the set first illumination light and second illumination light;
determine an analysis result related to presence or absence of an abnormal finding by analyzing a first image obtained by the image sensor when the first illumination light is irradiated and sets, based on the analysis result for the first image acquired by the image sensor when the first illumination light is irradiated, a combination of light in wavelength bands included in the second illumination light to be irradiated next;
set, as the first illumination light, green light and red light selected out of the light in the plurality of wavelength bands; and
analyze the first image to acquire, as the analysis result, an evaluation result relating to which of a color tone equivalent to the abnormal finding and a color tone equivalent to a normal finding a color tone of the first image belongs;
wherein, when a first evaluation result indicating that the color tone of the first image is equivalent to a color tone of a discolored mucous membrane is obtained, the one or more processors set, as the second illumination light, violet light, the green light, and the red light selected out of the light in the plurality of wavelength bands, when a second evaluation result indicating that the color tone of the first image is equivalent to a color tone of a reddened mucous membrane is obtained, the one or more processors set , as the second illumination light, blue light, the green light, and amber light selected out of the light in the plurality of wavelength bands, and, when a third evaluation result indicating that the color tone of the first image is equivalent to a color tone of a normal mucous membrane is obtained, the one or more processors set, as the second illumination light, the blue light, the green light, and the red light selected out of the light in the plurality of wavelength bands.

2. The endoscope system according to claim 1, wherein the one or more processors being further configured to, when the first evaluation result is obtained, generate an observation image using a violet component, a green component, and a red component included in a second image obtained by picking up an image of the object during irradiation of the second illumination light, when the second evaluation result is obtained, generate the observation image using a blue component, the green component, and an amber component included in the second image, and, when the third evaluation result is obtained, generate the observation image using the blue component, the green component, and the red component included in the second image.

3. The endoscope system according to claim 1, wherein, when a latest analysis result obtained by the one or more processors is different from a previous analysis result, the one or more processors being configured to set the second illumination light to correspond to the latest analysis result.

4. An endoscope system comprising:
a light source apparatus configured to be able to emit light in a plurality of wavelength bands to irradiate an object with illumination light;
an image sensor configured to pick up an image of return light from the object on which the illumination light is irradiated; and
one or more processors, each comprising hardware, the one or more processors being configured to:
set, as illumination light for illuminating the object including a biological tissue present in a subject, first illumination light obtained by combining light in one or more wavelength bands selected out of the light in the plurality of wavelength bands and second illumination light obtained by combining light in one or more wavelength bands different from the first illumination light, selected out of the light in the plurality of wavelength bands;
control the light source apparatus to alternately irradiate, from the light source apparatus, the set first illumination light and second illumination light;
determine an analysis result related to presence or absence of an abnormal finding by analyzing a first image obtained by the image sensor when the first illumination light is irradiated and sets, based on the analysis result for the first image acquired by the image sensor when the first illumination light is irradiated, a combination of light in wavelength bands included in the second illumination light to be irradiated next;
wherein the one or more processors being configured to set, as the first illumination light, violet light, green light, and red light selected out of the light in the plurality of wavelength bands, and
analyze the first image to acquire, as the analysis result, a judgement result relating to whether an abnormal finding region having a predetermined color tone is included in the first image;
wherein, when a first judgement result indicating that the abnormal finding region having the predetermined color tone is included in the first image is obtained, the one or more processors being configured to set, as the second illumination light, the violet light and amber light selected out of the light in the plurality of wavelength bands and, when a second judgement result indicating that the abnormal finding region having the predetermined color tone is not included in the first image is obtained, the one or more processors being configured to set , as the second illumination light, blue light and the amber light selected out of the light in the plurality of wavelength bands.

5. The endoscope system according to claim 4, wherein the one or more processors being further configured to, when the first judgement result is obtained, generate an observation image using a violet component and a green component included in the first image and the violet component and an amber component included in a second image obtained by picking up an image of the object during irradiation of the second illumination light and, when the second judgement result is obtained, generate the observation image using the violet component, the green component, and a red component included in the first image and a blue component and the amber component included in the second image.

6. The endoscope system according to claim 4, wherein, when a latest analysis result obtained by the one or more processors is different from a previous analysis result, the one or more processors being configured to set the second illumination light to correspond to the latest analysis result.

7. An endoscope system comprising:
a light source apparatus configured to be able to emit light in a plurality of wavelength bands to irradiate an object with illumination light;
an image sensor configured to pick up an image of return light from the object on which the illumination light is irradiated; and
one or more processors, each comprising hardware, the one or more processors being configured to:
set, as illumination light for illuminating the object including a biological tissue present in a subject, first illumination light obtained by combining light in one or more wavelength bands selected out of the light in the plurality of wavelength bands and second illumination light obtained by combining light in one or more wavelength bands different from the first illumination light, selected out of the light in the plurality of wavelength bands;
control the light source apparatus to alternately irradiate, from the light source apparatus, the set first illumination light and second illumination light;
determine an analysis result related to presence or absence of an abnormal finding by analyzing a first image obtained by the image sensor when the first illumination light is irradiated and sets, based on the analysis result for the first image acquired by the image sensor when the first illumination light is irradiated, a combination of light in wavelength bands included in the second illumination light to be irradiated next;
wherein the one or more processors being configured to set, as the first illumination light, violet light, green light, and red light selected out of the light in the plurality of wavelength bands, and
analyze the first image to acquire, as the analysis result, a judgement result relating to whether an abnormal finding region having a predetermined color tone is included in the first image;
wherein, when a first judgement result indicating that a biological tissue corresponding to the abnormal finding is included in the first image is obtained, the one or more processors being configured to set, as the second illumination light, the violet light selected out of the light in the plurality of wavelength bands and, when a second judgement result indicating that the biological tissue corresponding to the abnormal finding is not included in the first image is obtained, the one or more processors being configured to set, as the second illumination light, blue light and the amber light selected out of the light in the plurality of wavelength bands.

8. The endoscope system according to claim 7, wherein the one or more processors being further configured to, when the first judgement result is obtained, generate an observation image using a violet component and a green component included in the first image and the violet component included in a second image obtained by picking up an image of the object during irradiation of the second illumination light and, when the second judgement result is obtained, generate the observation image using the violet component, the green component, and a red component included in the first image and a blue component and an amber component included in the second image.

9. The endoscope system according to claim 7, wherein, when a latest analysis result obtained by the one or more processors is different from a previous analysis result, the one or more processors being configured to set the second illumination light to correspond to the latest analysis result.

10. An endoscope system comprising:
a light source apparatus configured to be able to emit light in a plurality of wavelength bands to irradiate an object with illumination light;
an image sensor configured to pick up an image of return light from the object on which the illumination light is irradiated; and
one or more processors, each comprising hardware, the one or more processors being configured to:
set, as illumination light for illuminating the object including a biological tissue present in a subject, first illumination light obtained by combining light in one or more wavelength bands selected out of the light in the plurality of wavelength bands and second illumination light obtained by combining light in one or more wavelength bands different from the first illumination light, selected out of the light in the plurality of wavelength bands;
control the light source apparatus to alternately irradiate, from the light source apparatus, the set first illumination light and second illumination light;
determine an analysis result related to presence or absence of an abnormal finding by analyzing a first image obtained by the image sensor when the first illumination light is irradiated and sets, based on the analysis result for the first image acquired by the image sensor when the first illumination light is irradiated, a combination of light in wavelength bands included in the second illumination light to be irradiated next;
wherein the illumination-light setting section sets, as the first illumination light, violet light, green light, and red light selected out of the light in the plurality of wavelength bands, and
the image analyzing section analyzes the first image to acquire, as the analysis result, an evaluation result relating to an atrophy degree of a mucous membrane included in the first image;
wherein, when a first evaluation result indicating that the atrophy degree of the mucous membrane included in the first image is a low degree or a medium degree is obtained, the one or more processors being configured to set, as the second illumination light, the violet light, the green light, and amber light selected out of the light in the plurality of wavelength bands and, when a second evaluation result indicating that the atrophy degree of the mucous membrane included in the first image is a high degree is obtained, the one or more processors being configured to set, as the second illumination light, blue light, the green light, and the amber light selected out of the light in the plurality of wavelength bands.

11. The endoscope system according to claim 10, wherein the one or more processors being further configured to, when the first evaluation result is obtained, generate an observation image using a violet component, a green component, and an amber component included in a second image obtained by picking up an image of the object during irradiation of the second illumination light and, when the second evaluation result is obtained, generate the observation image using the violet component and a red component included in the first image and a blue component, the green component, and the amber component included in the second image.

12. The endoscope system according to claim 10, wherein, when a latest analysis result obtained by the one or more processors is different from a previous analysis result, the one or more processors being configured to set the second illumination light to correspond to the latest analysis result.

13. An endoscope system comprising:
a light source apparatus configured to be able to emit light in a plurality of wavelength bands to irradiate an object with illumination light;
an image sensor configured to pick up an image of return light from the object on which the illumination light is irradiated; and
one or more processors, each comprising hardware, the one or more processors being configured to:
select, as illumination light for illuminating the object including a biological tissue present in a subject, light in combinations of one or more wavelength bands out of the light in the plurality of wavelength bands and set first illumination light and second illumination light formed by differentiating a ratio of the light in the combinations;
control the light source apparatus to alternately irradiate, from the light source apparatus, the first illumination light and the second illumination light set by the processor; and
determine an analysis result related to presence or absence of an abnormal finding by analyzing a first image obtained by the image sensor when the first illumination light is irradiated and set, based on the analysis result for the first image acquired by the image sensor when the first illumination light is irradiated, a light amount ratio of the light in the plurality of wavelength bands included in the second illumination light to be irradiated next;
wherein the one or more processors being configured to:
set, as the first light amount ratio, a light amount ratio for setting a ratio of violet light included in the first illumination light smaller than a ratio of blue light and setting a ratio of amber light included in the first illumination light smaller than a ratio of red light, and
analyze the first image to acquire, as the analysis result, an evaluation result relating to an atrophy degree of a mucous membrane included in the first image.

14. The endoscope system according to claim 13, wherein, when a first evaluation result indicating that the atrophy degree of the mucous membrane included in the first image is a low degree or a medium degree is obtained, the one or more processors being configured to set, as the second light amount ratio, a light amount ratio for setting a ratio of the blue light included in the second illumination light smaller than a ratio of the violet light and setting a ratio of the red light included in the second illumination light smaller than a ratio of the amber light and, when a second evaluation result indicating that the atrophy degree of the mucous membrane included in the first image is a high degree is obtained, set the second light amount ratio to a same light amount ratio as the first light amount ratio.

15. A method of controlling an endoscope system, the method comprising:
setting, as illumination light for illuminating an object including a biological tissue present in a subject, first illumination light obtained by combining light in one or more wavelength bands selected out of light in a plurality of wavelength bands and second illumination light obtained by combining light in one or more wavelength bands different from the first illumination light, selected out of the light in the plurality of wavelength bands;
controlling a light source apparatus configured to be emit light in the plurality of wavelength bands to irradiate the object with illumination light to alternately irradiate, from the light source apparatus, the set first illumination light and second illumination light;
determining an analysis result related to presence or absence of an abnormal finding by analyzing a first image obtained by an image sensor configured to pick up an image of return light from the object on which the illumination light is irradiated when the first illumination light is irradiated and setting, based on the analysis result for the first image acquired by the image sensor when the first illumination light is irradiated, a combination of light in wavelength bands included in the second illumination light to be irradiated next;
setting, as the first illumination light, green light and red light selected out of the light in the plurality of wavelength bands; and
analyzing the first image to acquire, as the analysis result, an evaluation result relating to which of a color tone equivalent to the abnormal finding and a color tone equivalent to a normal finding a color tone of the first image belongs;
wherein, when a first evaluation result indicating that the color tone of the first image is equivalent to a color tone of a discolored mucous membrane is obtained, the method sets, as the second illumination light, violet light, the green light, and the red light selected out of the light in the plurality of wavelength bands, when a second evaluation result indicating that the color tone of the first image is equivalent to a color tone of a reddened mucous membrane is obtained, the method sets, as the second illumination light, blue light, the green light, and amber light selected out of the light in the plurality of wavelength bands, and, when a third evaluation result indicating that the color tone of the first image is equivalent to a color tone of a normal mucous membrane is obtained, the method sets, as the second illumination light, the blue light, the green light, and the red light selected out of the light in the plurality of wavelength bands.

16. A method of controlling an endoscope system, the method comprising:
setting, as illumination light for illuminating an object including a biological tissue present in a subject, first illumination light obtained by combining light in one or more wavelength bands selected out of light in a plurality of wavelength bands and second illumination light obtained by combining light in one or more wavelength bands different from the first illumination light, selected out of the light in the plurality of wavelength bands;
controlling a light source apparatus configured to be emit light in the plurality of wavelength bands to irradiate the object with illumination light to alternately irradiate, from the light source apparatus, the set first illumination light and second illumination light;

determining an analysis result related to presence or absence of an abnormal finding by analyzing a first image obtained by an image sensor configured to pick up an image of return light from the object on which the illumination light is irradiated when the first illumination light is irradiated and setting, based on the analysis result for the first image acquired by the image sensor when the first illumination light is irradiated, a combination of light in wavelength bands included in the second illumination light to be irradiated next;

setting, as the first illumination light, violet light, green light, and red light selected out of the light in the plurality of wavelength bands, and analyzing the first image to acquire, as the analysis result, a judgement result relating to whether an abnormal finding region having a predetermined color tone is included in the first image;

wherein, when a first judgement result indicating that the abnormal finding region having the predetermined color tone is included in the first image is obtained, the method sets, as the second illumination light, the violet light and amber light selected out of the light in the plurality of wavelength bands and, when a second judgement result indicating that the abnormal finding region having the predetermined color tone is not included in the first image is obtained, the method sets, as the second illumination light, blue light and the amber light selected out of the light in the plurality of wavelength bands.

17. A method of controlling an endoscope system, the method comprising:

setting, as illumination light for illuminating an object including a biological tissue present in a subject, first illumination light obtained by combining light in one or more wavelength bands selected out of light in a plurality of wavelength bands and second illumination light obtained by combining light in one or more wavelength bands different from the first illumination light, selected out of the light in the plurality of wavelength bands;

controlling a light source apparatus configured to be emit light in the plurality of wavelength bands to irradiate the object with illumination light to alternately irradiate, from the light source apparatus, the set first illumination light and second illumination light;

determining an analysis result related to presence or absence of an abnormal finding by analyzing a first image obtained by an image sensor configured to pick up an image of return light from the object on which the illumination light is irradiated when the first illumination light is irradiated and setting, based on the analysis result for the first image acquired by the image sensor when the first illumination light is irradiated, a combination of light in wavelength bands included in the second illumination light to be irradiated next;

setting, as the first illumination light, violet light, green light, and red light selected out of the light in the plurality of wavelength bands, and analyzing the first image to acquire, as the analysis result, a judgement result relating to whether an abnormal finding region having a predetermined color tone is included in the first image;

wherein, when a first judgement result indicating that a biological tissue corresponding to the abnormal finding is included in the first image is obtained, the method sets, as the second illumination light, the violet light selected out of the light in the plurality of wavelength bands and, when a second judgement result indicating that the biological tissue corresponding to the abnormal finding is not included in the first image is obtained, the method sets, as the second illumination light, blue light and the amber light selected out of the light in the plurality of wavelength bands.

18. A method of controlling an endoscope system, the method comprising:

setting, as illumination light for illuminating an object including a biological tissue present in a subject, first illumination light obtained by combining light in one or more wavelength bands selected out of light in a plurality of wavelength bands and second illumination light obtained by combining light in one or more wavelength bands different from the first illumination light, selected out of the light in the plurality of wavelength bands;

controlling a light source apparatus configured to be emit light in the plurality of wavelength bands to irradiate the object with illumination light to alternately irradiate, from the light source apparatus, the set first illumination light and second illumination light;

determining an analysis result related to presence or absence of an abnormal finding by analyzing a first image obtained by an image sensor configured to pick up an image of return light from the object on which the illumination light is irradiated when the first illumination light is irradiated and setting, based on the analysis result for the first image acquired by the image sensor when the first illumination light is irradiated, a combination of light in wavelength bands included in the second illumination light to be irradiated next;

setting, as the first illumination light, violet light, green light, and red light selected out of the light in the plurality of wavelength bands, and analyzing the first image to acquire, as the analysis result, an evaluation result relating to an atrophy degree of a mucous membrane included in the first image;

wherein, when a first evaluation result indicating that the atrophy degree of the mucous membrane included in the first image is a low degree or a medium degree is obtained, the method sets, as the second illumination light, the violet light, the green light, and amber light selected out of the light in the plurality of wavelength bands and, when a second evaluation result indicating that the atrophy degree of the mucous membrane included in the first image is a high degree is obtained, the method sets, as the second illumination light, blue light, the green light, and the amber light selected out of the light in the plurality of wavelength bands.

19. A method of controlling an endoscope system, the method comprising:

selecting, as illumination light for illuminating an object including a biological tissue present in a subject, light in combinations of one or more wavelength bands out of the light in the plurality of wavelength bands and set first illumination light and second illumination light formed by differentiating a ratio of the light in the combinations;

controlling the light source apparatus to alternately irradiate, from the light source apparatus, the first illumination light and the second illumination light set by the processor; and determine an analysis result related to presence or absence of an abnormal finding by analyzing a first image obtained by an image sensor configured to pick up an image of return light from the object on which the illumination light is irradiated when the first illumination light is irradiated and setting, based on the analysis result for the first image acquired by the image sensor when the first illumination light is irradiated, a light amount ratio of the light in the plurality of wavelength bands included in the second illumination light to be irradiated next;

wherein the method further comprising:
   setting, as the first light amount ratio, a light amount ratio for setting a ratio of violet light included in the first illumination light smaller than a ratio of blue light and setting a ratio of amber light included in the first illumination light smaller than a ratio of red light, and analyzing the first image to acquire, as the analysis result, an evaluation result relating to an atrophy degree of a mucous membrane included in the first image.

\* \* \* \* \*